US009888636B2

(12) United States Patent
Bai et al.

(10) Patent No.: US 9,888,636 B2
(45) Date of Patent: Feb. 13, 2018

(54) SOYBEAN MARKERS LINKED TO SCN RESISTANCE

(75) Inventors: Yonghe Bai, Westfield, IN (US); Fang Lu, Westfield, IN (US); Thomas W. Greene, West Des Moines, IA (US); Robert E. Moore, Gibson City, IL (US); Bradley Hedges, Kingsville (CA); Siva P. Kumpatla, Carmel, IN (US); Raghav Ram, Carmel, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 1080 days.

(21) Appl. No.: 13/287,848

(22) Filed: Nov. 2, 2011

(65) Prior Publication Data
US 2012/0131693 A1 May 24, 2012

Related U.S. Application Data

(60) Provisional application No. 61/410,783, filed on Nov. 5, 2010.

(51) Int. Cl.
*C12Q 1/68* (2006.01)
*A01H 1/04* (2006.01)
*A01H 5/10* (2006.01)

(52) U.S. Cl.
CPC ............... *A01H 1/04* (2013.01); *A01H 5/10* (2013.01); *C12Q 1/6895* (2013.01); *C12Q 2600/13* (2013.01)

(58) Field of Classification Search
USPC ........ 800/260, 266, 267, 279, 312; 435/468; 536/24.3
See application file for complete search history.

(56) References Cited

U.S. PATENT DOCUMENTS

| | | |
|---|---|---|
| 5,491,081 A | 2/1996 | Webb |
| 6,096,944 A | 8/2000 | Vierling et al. |
| 6,162,967 A | 12/2000 | Webb |
| 6,271,437 B1 | 8/2001 | Jessen et al. |
| 6,284,948 B1 | 9/2001 | Jessen et al. |
| 6,300,541 B1 | 10/2001 | Lightfoot et al. |
| 6,538,175 B1 | 3/2003 | Webb |
| 7,154,021 B2 | 12/2006 | Hauge et al. |
| 7,485,770 B2 | 2/2009 | Hauge et al. |
| 2002/0129402 A1 | 9/2002 | Lightfoot et al. |
| 2002/0144310 A1 | 10/2002 | Lightfoot et al. |
| 2003/0005491 A1 | 1/2003 | Hauge et al. |
| 2003/0135881 A1 | 7/2003 | Webb |
| 2006/0225150 A1 | 10/2006 | Hauge et al. |
| 2006/0253919 A1 | 11/2006 | Hauge et al. |
| 2008/0072352 A1 | 3/2008 | Lightfoot et al. |
| 2009/0100537 A1 | 4/2009 | Concibido et al. |

FOREIGN PATENT DOCUMENTS

| | | |
|---|---|---|
| WO | WO95/20669 | 8/1995 |
| WO | WO01/51627 | 7/2001 |
| WO | 200233106 | 4/2002 |
| WO | WO2008153804 | 12/2008 |
| WO | 2009048847 | 4/2009 |

OTHER PUBLICATIONS

Hadley et. al (1980)., in Hybridization in Crop Plants, ed. Fehr & Hadley, Society of Agronomy and Crop Science Society of America, Madison, Wisconsin, p. 133.*
Fourgoux-Nicol et al. (1999). Plant Molecular Biology 40: 857-872.*
Lewers et al (Genome (2001), 40(6), pp. 1057-1064).*
International Search Report for PCT/US2011/058986, dated Jul. 2, 2012.
Written Opinion for PCT/US2011/058986, dated Jul. 2, 2012.
B. X. Qiu, et al., "RFLP markers associated with soybean cyst nematode resistance and seed composition in a 'Peking' X 'Essex' population", Theor Appl Genet, 1999, pp. 356-364, vol. 98.
Webb, et al., "Genetic mapping of soybean cyst nematode race-3 resistance loci n the soybean PI 437.654" Theor Appl Genet, 1995, p. 574-581, vol. 91.
Li et al., "Development of SNP marker and haplotype analysis of the candidate gee for rhg1, which confers resistance to soybean cyst nematode in soybean," Mol .Breeding, 2009, pp. 63-76, vol. 24.
Concibido, et al., "A decade fo QTL mapping for cyst nematode resistance in soybean," Crop Science, Jul.-Aug. 2004, pp. 1121-1131, vol. 44.
Graham, et al., "Organization, Expression and evolution of a disease resistance gene cluster in soybean," Genetics Society America, 2002, pp. 1961-1977.
Wu, et al., "QTL, additive and epistatic effects for SCN resistance in PI 437654," Theor Appl Genet, 2009, pp. 1093-1105, vol. 11.
Meksem, et al., "High-throughput genotyping for a polymorphism linked to soybean cyst nematode resistance gent Rhg4, by using TaqmanTM probes," Molecula Breeding, 2001, pp. 63-71, vol. 7.
Meksem, et al., "Clustering among loci underlying soybean resistance to Fusarium solani, SDS and SCN in near-isogenic lines," Theor Appl Genet, 1999, pp. 1131-1142, vol. 99.
Shannon et al. (Crop Sci 45: 1673-1674).
Shannon et al. (Crop Sci 45: 1673-1674), 2005.
Wang et al. (Theor Appl Genet 103: 561-566, 2001).

* cited by examiner

*Primary Examiner* — Medina A Ibrahim
(74) *Attorney, Agent, or Firm* — James Daly, IV; Magleby Cataxinos & Greenwood

(57) ABSTRACT

This disclosure concerns compositions and methods for identifying the SCN resistant phenotype in soybean. In some embodiments, the disclosure concerns methods for performing marker-assisted breeding and selection of plants carrying one or more determinants of SCN resistance in soybean.

11 Claims, 12 Drawing Sheets

| LG | Gene | Race | Peak marker/interval | Source | Reference |
|---|---|---|---|---|---|
| A1 | unknown | 3 | A487 | Peking, PI 437654 | Theor. Appl. Genet. 92:83–88 |
| A1 | unknown | 2 | A262-Satt300 | PI 438489B | Theor. Appl. Genet. 102:921–928 |
| A2 | Rhg4 | not available | pBLT24, pBLT65 | not available | Theor. Appl. Genet. 85:136–136 |
| A2 | Rhg4 | 3 | pBLT65a | Peking | Crop Sci. 37:965–971 |
| A2 | Rhg4 | 3 | i locus | Peking | Breed. Sci. 45:435–443 |
| A2 | Rhg4 | 3 | EccgMcac406 | Peking | Theor. Appl. Genet. 103:710–717 |
| A2 | Rhg4 | 1,3 | SCAR548/563 | Peking, PI 88788, | Mol. Breed. 4:359–367 |
| A2 | Rhg4 | 3 | A085 | PI 209332 | Crop Sci. 34:240–246 |
| A2 | Rhg4 | 3 | i locus | PI 437654 | Theor. Appl. Genet. 91:574–581 |
| A2 | Rhg4 | 1,3 | pBLT65a | PI 437654 | U.S. Patent 6,538,175 B1 |
| A2 | unknown | 1 | Satt187-AW133402 | Essex, PI437654 | Theor. Appl. Genet. 118:1093–1105 |
| A2 | unknown | 3 | EaacMcac086_Satt187 | Essex, PI437654 | Theor. Appl. Genet. 118:1093–1105 |
| A2 | Rhg4 | 1,3 | Satt424-Satt632- | PI 404198A | Crop Sci. 46:224–233 |
| A2 | | 3 | Sat_400-Satt424 | PI 90763 | Theor. Appl. Genet. 111:965–971 |
| B1 | unknown | 3 | A006 | Peking, PI 437654 | Theor. Appl. Genet. 92:83–88 |
| B1 | unknown | 1,2,5 | A006-Satt583 | PI 89772 | Crop Sci. 41:1589–1595 |
| B1 | | 1,5 | Satt605-EacaMct087 | Essex, PI437654 | Theor. Appl. Genet. 118:1093–1105 |
| B1 | | 3,1 | EacaMct087-Satt484 | Essex, PI437654 | Theor. Appl. Genet. 118:1093–1105 |
| B1 | | 2,5 | Satt453 | PI 404198A | Crop Sci. 46:224–233 |
| B1 | | 2,5 | Satt453-Satt359 | PI 90763 | Theor. Appl. Genet. 111:965–971 |
| B1 | unknown | 1,2,5 | Satt583-Sat_123 | PI 438489B | Theor. Appl. Genet. 102:921–928 |
| B1 | unknown | 1,2,5,14 | A567a | PI 437654 | U.S. Patent 6,538,175 B1 |
| B1 | unknown | 3 | A567 | Peking, PI 437654 | Theor. Appl. Genet. 92:83–88 |
| B2 | unknown | 1,3 | A593 | Peking | Theor. Appl. Genet. 98:368–384 |
| B2 | unknown | 1,3 | Satt168-A329 | PI438489B | Theor. Appl. Genet. 102:921–928 |
| C1 | unknown | 2,14 | A463-Satt396 | PI438489B | Theor. Appl. Genet. 102:921–928 |
| C1 | unknown | 1,2 | php02298b | PI 437654 | U.S. Patent 6,538,175 B1 |
| C1 | | 3 | Sat_140-EaacMctc178 | Essex, PI437654 | Theor. Appl. Genet. 118:1093–1105 |
| C2 | unknown | 3 | A121_1 | A81-356022 | Theor. Appl. Genet. 103:561–566 |
| C2 | unknown | 3 | A635 | Peking | Breeding Sci. 45:435–443 |

*FIG. 1a*

| LG | Gene | Race | Peak marker/interval | Source | Reference |
|---|---|---|---|---|---|
| C2 | unknown | 14 | A428 | Peking, PI 88788 | Mol. Breed. 4:359-367 |
| C2 | unknown | 1,5 | Satt371-Satt202 | PI 437654 | Theor. Appl. Genet. 102:921-928 |
| D1a | unknown | 3,5,14 | A398-K487 | PI 437654 | Theor. Appl. Genet. 102:921-928 |
| D1a | unknown | 5 | Satt342-Satt368 | PI 89772 | Crop Sci. 41:1589-1595 |
| D1a | unknown | 2 | AW781285-Sat_3-8 | Essex, PI 437654 | Theor. Appl. Genet. 118:1093-1105 |
| D1a | unknown | 3 | Sat_272_2-Satt129 | Essex, PI 437654 | Theor. Appl. Genet. 118:1093-1105 |
| D2 | unknown | 14 | Satt082 | Peking, PI 437654 | Theor. Appl. Genet. 102:91-96 |
| D2 | unknown | 5 | A064-2 | PI 209332 | Crop Sci. 36:1643-1650 |
| D2 | unknown | 1 | B132-Satt372 | PI 89772 | Crop Sci. 41:1589-1595 |
| E | unknown | 2,14 | A656-Satt452 | PI 437654 | Theor. Appl. Genet. 102:921-928 |
| E | unknown | 3 | Bng107_1-A458_1 | PI 468916 | Theor. Appl. Genet. 103:561-566 |
| E | unknown | 3 | A135-Satt231 | PI 89772 | Crop Sci. 41:1589-1595 |
| E | | 5 | Satt573-Satt204 | PI 90763 | Theor. Appl. Genet. 111:965-971 |
| E | | | EaggMcg125-EaccMtc230 | PI 468916 | Crop Sci. 45:2473-2481 |
| F | unknown | 3 | G15 | Peking | Breed. Sci. 46:435-443 |
| F | unknown | 3 | A112 | Peking, PI 437654 | Theor. Appl. Genet. 92:83-88 |
| F | unknown | 1,5 | K003 | Peking, PI 88788 | Mol. Breed. 4:359-367 |
| G | rhg1 | 3 | K069 | PI 209332 | Crop Sci. 34:240-246 |
| G | rhg1 | 3 | OIO3458 | Peking | Crop Sci. 37:965-971 |
| G | rhg1 | 1,3,6 | CK6 | Peking | Crop Sci. 37:258-264 |
| G | unknown | 1,3,6 | A378 | Peking | Crop Sci. 37:258-264 |
| G | rhg1 | 3 | EatgMcga87 | Peking | Theor. Appl. Genet. 103:710-717 |
| G | rhg1 | 3 | Satt038 | Peking, PI 437654 | Crop Sci. 39:982-987 |
| G | rhg1 | 1,3 | K069 | Peking, PI 88788 | Mol. Breed. 4:359-367 |
| G | rhg1 | 1,3,6 | CK6 | PI 209332 | Crop Sci. 36:1643-1650 |
| G | rhg1 | 3 | php05354a | PI 437654 | Theor. Appl. Genet. 91:574-581 |
| G | rhg1 | 1,2,3,5,14 | php05354a | PI 437654 | U.S. Patent 6,538,175 B1 |
| G | unknown | 1,2,3,5 | Satt130-Satt012 | PI 437654 | Theor. Appl. Genet. 102:921-928 |
| G | unknown | 3 | Satt288-Satt472 | PI 468916 | Theor. Appl. Genet. 103:561-566 |
| G | rhg1 | 3,6 | CK6 | PI 88788 | Crop Sci. 37:258-264 |
| G | rhg1 | 1,2,3,5 | B053-Satt309 | PI 89772 | Crop Sci. 41:1589-1595 |

*FIG. 1b*

| LG | Gene | Race | Peak marker/interval | Source | Reference |
|---|---|---|---|---|---|
| G | rhg1 | 1,3,6 | C006 | PI 90763 | Crop Sci. 37:258-264 |
| G | rhg1 | 1 | Satt309-Rhg1-Indel | Essex x PI437654 | Theor. Appl. Genet. 118:1093-1105 |
| G | rhg1 | 2,3,5 | Rhg1-Indel-Satt235 | Essex x PI437654 | Theor. Appl. Genet. 118:1093-1105 |
| G | | Chatham(7) | Satt533-Satt517 | G. max | Theor. Appl. Genet. 114:461-472 |
| G | rhg1 | 1 | Satt309-Satt688 | PI 404198A | Crop Sci. 46:224-233 |
| G | rhg1 | 2,5 | Satt163-Satt309 | PI 404198A | Crop Sci. 46:224-233 |
| G | | 2,3,5 | Satt163-Satt688 | PI 90763 | Theor. Appl. Genet. 111:965-971 |
| G | | | EcaaMtac72-Satt472 | PI 468916 | Crop Sci. 45: 2473-2481 |
| G | | | eagcMaag176-Satt288 | PI 468916 | Crop Sci. 45: 2473-2481 |
| H | unknown | 1,3 | B072 | Peking | Theor. Appl. Genet. 98:356-364 |
| H | | 1 | Satt009-Satt541 | Essex, PI437654 | Theor. Appl. Genet. 118:1093-1105 |
| I | unknown | 5 | K011 | Peking | Theor. Appl. Genet. 98:356-364 |
| I | | Ruthven(7) | Satt102-Satt148 | S. soja | Theor. Appl. Genet. 114:461-472 |
| I | | 3,5,14 | Sat_299-Sct_189 | Essex, PI437654 | Theor. Appl. Genet. 118:1093-1105 |
| I | | Chatham | Satt162-Satt330 | G. soja | Theor. Appl. Genet. 114:461-472 |
| J | unknown | 3 | B032 | PI 209332 | Crop Sci. 34:240-246 |
| J | unknown | 3 | B032 | PI 209332 | Crop Sci. 36:1643-1650 |
| J | unknown | 3 | B032 | PI 90763 | Crop Sci. 37:258-264 |
| J | unknown | 2,14 | K079 | PI 437654 | U.S. Patent 6,538,175 B1 |
| J | | 2,3 | Satt547-Sat_224 | PI 90763 | Theor. Appl. Genet. 111:965-971 |
| L | unknown | 1 | A023 | PI 209332 | Crop Sci. 36:1643-1650 |
| L | | 3 | Sat_286-Satt229 | PI 90763 | Theor. Appl. Genet. 111:965-971 |
| M | unknown | 1,3,5 | A131 | Peking, PI 88788 | Mol. Breed. 4:359-367 |
| M | unknown | 3 | php020301a | PI 437654 | Theor. Appl. Genet. 91:574-581 |
| M | unknown | 1,3,5,14 | php020301a | PI 437654 | U.S. Patent 6,538,175 B1 |
| N | unknown | 6 or 3? | A280 | Peking | Crop Sci. 37:258-264 |
| N | | 5 | Sat_280-Satt549 | PI 404198A | Crop Sci. 46:224-233 |
| K | | 1 | Satt552-Satt499 | Essex, PI437654 | Theor. Appl. Genet. 118:1093-1105 |
| K | | Chatham | Satt260-Satt196 | G. soja | Theor. Appl. Genet. 114:461-472 |
| O | | Ruthven | Satt173-Satt468 | G. soja | Theor. Appl. Genet. 114:461-472 |

*FIG. 1c*

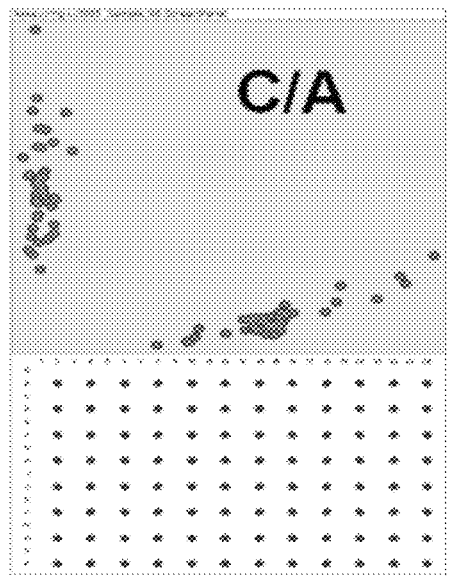
rhg1_3995
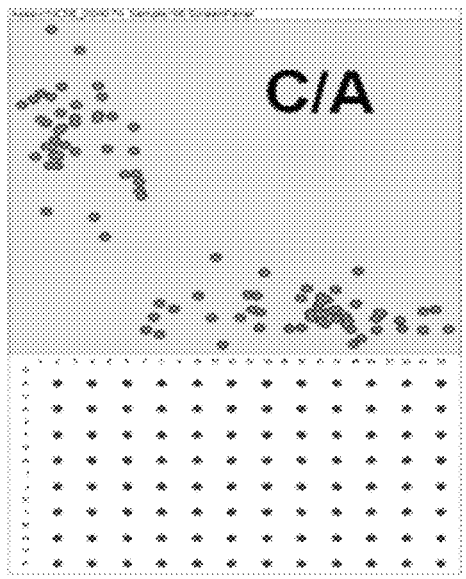
NCSB_004074
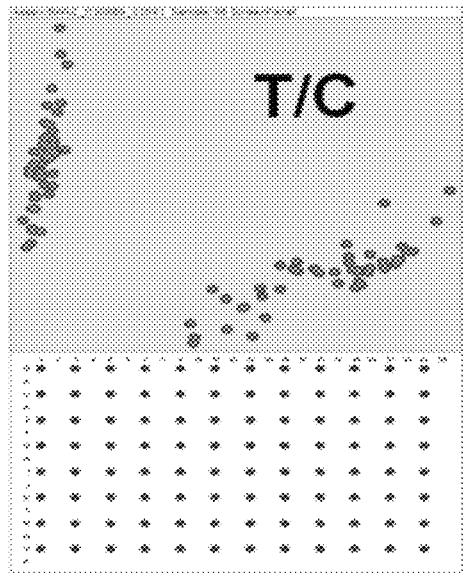
BARC_010889_01691
LG G (Gm 18)
FIG. 8

SEQUENCE LISTING

```
<160> NUMBER OF SEQ ID NOS: 12

<210> SEQ ID NO 1
<211> LENGTH: 51
<212> TYPE: DNA
<213> ORGANISM: Artificial
<220> FEATURE:
<223> OTHER INFORMATION: rhg1-3995 primer

<400> SEQUENCE: 1
gaaggtgacc aagttcatgc tggaattatg ttgggttttt tttctttctg t         51

<210> SEQ ID NO 2
<211> LENGTH: 50
<212> TYPE: DNA
<213> ORGANISM: Artificial
<220> FEATURE:
<223> OTHER INFORMATION: rhg1-3995 primer

<400> SEQUENCE: 2
gaaggtcgga gtcaacggat tgaattatgt tgggtttttt ttctttctgg          50

<210> SEQ ID NO 3
<211> LENGTH: 29
<212> TYPE: DNA
<213> ORGANISM: Artificial
<220> FEATURE:
<223> OTHER INFORMATION: rhg1-3995 primer

<400> SEQUENCE: 3
gcccagaaaa aagggataaa taacggata                                 29

<210> SEQ ID NO 4
<211> LENGTH: 51
<212> TYPE: DNA
<213> ORGANISM: Artificial
<220> FEATURE:
<223> OTHER INFORMATION: NCSB_004074 primer

<400> SEQUENCE: 4
gaaggtgacc aagttcatgc tattatgttg taacacaaat ttgcacctca t        51

<210> SEQ ID NO 5
<211> LENGTH: 48
<212> TYPE: DNA
<213> ORGANISM: Artificial
<220> FEATURE:
<223> OTHER INFORMATION: NCSB_004074 primer

<400> SEQUENCE: 5
gaaggtcgga gtcaacggat tatgttgtaa cacaaatttg cacctcag            48
```

```
<210> SEQ ID NO 6
<211> LENGTH: 30
<212> TYPE: DNA
<213> ORGANISM: Artificial
<220> FEATURE:
<223> OTHER INFORMATION: NCSB_004074 primer

<400> SEQUENCE: 6
ctatacaact aaatcgtaat tccattgtat                                       30

<210> SEQ ID NO 7
<211> LENGTH: 54
<212> TYPE: DNA
<213> ORGANISM: Artificial
<220> FEATURE:
<223> OTHER INFORMATION: BARC_010889-01691 primer

<400> SEQUENCE: 7
gaaggtgacc aagttcatgc tgaaaaaata aaattgatca tcacatatgg ttag           54

<210> SEQ ID NO 8
<211> LENGTH: 54
<212> TYPE: DNA
<213> ORGANISM: Artificial
<220> FEATURE:
<223> OTHER INFORMATION: BARC_010889-01691 primer

<400> SEQUENCE: 8
gaaggtcgga gtcaacggat tgaaaaaata aaattgatca tcacatatgg ttaa           54

<210> SEQ ID NO 9
<211> LENGTH: 30
<212> TYPE: DNA
<213> ORGANISM: Artificial
<220> FEATURE:
<223> OTHER INFORMATION: BARC_010889-01691 primer

<400> SEQUENCE: 9
taagtgaggg caatgtatta gtatyaagta                                      30

<210> SEQ ID NO 10
<211> LENGTH: 121
<212> TYPE: DNA
<213> ORGANISM: Glycine max

<400> SEQUENCE: 10
cacgattttg ttgtgttaca taaattacta tacaactaaa tcgtaattcc attgtattac    60
mtgaggtgca aatttgtgtt acaacataat tgtaatttta ttgtacgata aaactataa    120 c                                                                    121

<210> SEQ ID NO 11
<211> LENGTH: 189
<212> TYPE: DNA
<213> ORGANISM: Glycine max
<220> FEATURE:
<221> NAME/KEY: misc_feature
<222> LOCATION: (92)..(92)
<223> OTHER INFORMATION: n is a, c, g, or t

<400> SEQUENCE: 11
ctcttcacac ctttaaggaa gttagtacca ttccactatt caagtatttt ttttaattca    60
aaattattaa gtgagggcaa tgtattagta tnaagtayta accatatgtg atgatcaatt  120 ttatttttc atggctttgt cgaaagtaac attatattgt ggtttttaaat gaaaatctgt  180
```

```
gatttgcat                                                                      189

<210> SEQ ID NO 12
<211> LENGTH: 490
<212> TYPE: DNA
<213> ORGANISM: Glycine max

<400> SEQUENCE: 12
tctgataact atgacagcat cttccaagat aatgacttcc aagttccaac actggctctg    60
tacatttgaa ctaattttat atcatttatc tattgtgatt gaaatataaa attgaagtga   120
tgtgaacaat acaaatcaca tcttgaatta aaatatctaa caactggaac aaataagagg   180
cccagaaaaa agggataaat aacggataac aagmcagaaa gaaaaaaaac ccaacataat   240
tccaacttca aaattcactc aataaaaagt ttaacatgta aatttacttg gaaacaaaac   300
tcataaccaa taataataat aataaaagaa atcagtttta tagcattaat ttgggatgct   360
ctgcttgtat gcaaatggca caaccttacc ctcaagattg caaaacacag atgagtaaca   420
gatgcaatgt gaatcaataa aaagtattgt tgcgttgttg atgacacaac cttactcata   480
aaaaatgcat                                                          490
```

SOYBEAN MARKERS LINKED TO SCN RESISTANCE

CROSS-REFERENCE TO RELATED APPLICATION

This application is a continuation of U.S. patent application Ser. No. 13/287,819 (now U.S. Pat. No. 9,049,822), filed on Nov. 2, 2011, which application claims the benefit of U.S. Provisional Patent Application Ser. No. 61/410,783, filed Nov. 5, 2010, the disclosure of each of which is hereby incorporated in its entirety by this reference.

TECHNICAL FIELD

The present disclosure relates to plant disease resistance. In some embodiments, the disclosure relates to Soybean cyst nematode (SCN) resistance in soybean. In particular embodiments, the disclosure relates to compositions and methods for identifying an SCN resistance trait in an organism, for example, molecular markers that are tightly linked to SCN resistance. Further embodiments relate to compositions and methods for introducing an SCN resistance trait into a host organism, for example, by using molecular markers tightly linked to SCN resistance.

BACKGROUND

The soybean, *Glycine max*, is one of the major economic crops grown worldwide as a primary source of vegetable oil and protein. Growing demand for low cholesterol and high fiber diets has increased soybean's importance as a food. Over 10,000 soybean varieties have now been introduced into the United States, of which a limited number form the genetic base of cultivars developed from hybridization and selection programs. Johnson and Bernard, The Soybean, Norman Ed., Academic Press, N.Y., pp. 1-73, 1963.

Soybean cyst nematode, (SCN, *Heterodera glycines* (HG) Ichinohe) is the single most damaging pest affecting soybean in the U.S. as well as in most of the other top soybean-producing countries of the world. The estimated yield reduction in the United States was between approximately 2.9 and 3.4 million tons in 2003 and 2004, which resulted in an estimated annual loss of approximately $1.5 billion. Wrather et al. (2001); Wrather and Koenning (2006). The SCN phenotype is a very complex trait, which is controlled by multiple genes, both recessive and dominant. Concibido et al. (2004). SCN phenotyping is time consuming, cost and labor intensive.

SCN infection causes various symptoms that may include chlorosis of the leaves and stems, root necrosis, loss in seed yield, and suppression of root and shoot growth. The above-ground symptoms of SCN infection are not unique to SCN infection, and could be confused with nutrient deficiency, particularly iron deficiency, stress from drought, herbicide injury or another disease. The first signs of infection are groups of plants with yellowing leaves that have stunted growth. The pathogen may also be difficult to detect on the roots, since stunted roots are also a common symptom of stress or plant disease. Adult females and cysts of SCN are about ⅟32 inch long and, thus, visible without magnification. Observation of adult females and cysts on the roots is the only accurate way to detect and diagnose SCN infection in the field.

The presence of SCN is usually not obvious at the time of initial soil infestation. The SCN population density must increase in the soil until it is sufficient to cause above-ground symptoms on plants or a decrease in yield. Population densities may take several years to reach significant numbers. Thus, current SCN damage is the result of infestations that have been growing for several years. Although soybean is the primary host of SCN, other legumes can serve as hosts, for example: green beans, snap beans, dry beans, red beans, lima beans, mung beans, bush beans, Adzuki beans, garden peas, and cowpeas. There are thirty days in the SCN life cycle. Thus, a single growing season encompasses multiple generations of the parasite. Moreover, SCN eggs may remain intact in soil for several years before hatching.

In the past, an SCN population was given a ""race"" designation by comparing its reproduction on a set of four soybean germplasm lines with that on a standard SCN-susceptible soybean cultivar. The most commonly used race scheme identified 16 races of SCN. The race designation allowed nematologists and soybean breeders to share information about the ability of certain SCN populations to reproduce on soybean varieties that contain certain genes for resistance to SCN.

In 2003, the HG Type Test was developed to replace the race test. This new test includes seven sources of resistance (germplasm lines) and the results are shown as a percentage, indicating how much the nematode population from a soil sample increased on each of the seven lines. This test indicates which sources of resistance would be good for a particular field being tested, and which would be poor. Since the genetic sources of resistance are currently limited in commercially available soybean varieties, it is important to rotate these ""sources of resistance"" to delay the build-up of a virulent SCN population.

Shortly after the discovery of SCN in the United States, sources of SCN resistance were identified. Ross and Brim (1957) *Plant Dis. Rep.* 41:923-4. Some lines, such as Peking and PI 88788, were quickly incorporated into breeding programs. Peking became widely used as a source of resistance due to its lack of agronomically undesirable traits, with Pickett as the first SCN resistant cultivar released. The recognition that certain SCN resistant populations could overcome resistant cultivars led to an extensive screen for additional sources of SCN resistance. PI 88788 emerged as a popular source of race 3 and 4 resistance, even though it had a cyst index greater than 10% (but less than 20%) against race 4, and Peking and its derivatives emerged as a popular source for races 1 and 3. PI 437654 was subsequently identified as having resistance to all known races and its SCN resistance was backcrossed into Forrest. Currently, there are more than 130 PIs known to have SCN resistance. PI 209332 and PI 90763 are other exemplary SCN resistant soybean breeding lines. Not all varieties with the same source of resistance have comparable yields, nor do they respond identically to SCN.

Resistant soybean varieties are the most effective tool available for management of SCN. SCN densities usually decrease when resistant soybeans are grown because most SCN juveniles are unable to feed and develop on the roots of the resistant varieties. However, in any naturally infested field, a few SCN juveniles (<1%) will be able to reproduce on the resistant varieties currently available. The number of SCN juveniles that can reproduce on resistant soybean varieties can increase when resistant varieties are grown repeatedly. Eventually, the SCN population may be able to reproduce as well on a resistant variety as a susceptible variety if SCN-resistant soybeans are grown every time soybeans are produced in an infested field. Fortunately, the number of SCN juveniles that can reproduce on resistant varieties declines when susceptible soybean varieties are grown because these nematodes do not compete well for food with the other SCN juveniles in the soil that cannot feed on the resistant varieties.

SCN race 3 is considered to be the most prominent race in the Midwestern soybean producing states. Considerable effort has been devoted to the genetics and breeding for resistance to race 3. While both Peking and PI 88788 are resistant to SCN race 3, classical genetics studies suggest that they harbor different genes for race 3 resistance. Rao-Arelli and Anand (1988) *Crop Sci.* 28:650-2. Race 3 resistance is probably under the control of three or four different genes. Id.; see also Mansur et al. (1993) *Crop Sci.* 33:1249-53. One major SCN resistance QTL that maps to linkage group G is rhg1. Concibido et al. (1996) *Theor. Appl. Genet.* 93:234-41. Other SCN resistance QTLs map to linkage groups A2, C1, M, D, J, L25, L26, and K. Id.; U.S. Pat. No. 5,491,081. SCN resistance QTLs behave in a race-specific manner, at least by accounting for different proportions of the total phenotypic variation with respect to different SCN races. Concibido et al. (1997) *Crop Sci.* 37:258-64. However, the rhg1 locus on linkage group G may be necessary for the development of resistance to any of the identified SCN races. But see Qui et al. (1999) *Theor. Appl. Genet.* 98:356-64.

Markers that are linked to SCN traits include RFLPs, SSRs and SNPs. The SNP markers identified in this disclosure can be used to do SCN genotyping to support a breeding program. Using the presently disclosed SNP markers to perform SCN genotyping in support of a breeding program provides: cost and time savings, early selection of desired progeny, and more accurate and rapid commercialization of SCN resistant soybean varieties.

DISCLOSURE

Molecular markers that are linked to an SCN phenotype may be used to facilitate marker-assisted selection for the SCN resistance trait in soybean. Marker-assisted selection provides significant advantages with respect to time, cost, and labor, when compared to SCN phenotyping. Surprisingly, it is disclosed herein that among 15 SNP markers identified to be within or near SCN disease resistance QTL regions in the soybean genome that were polymorphic in parent genotypes, only three were linked to the SCN resistance trait. These three SNP markers, then, offer superior utility in marker-assisted selection of SCN resistant soybean varieties.

Described herein are nucleic acid molecular markers that are linked to (e.g., linked, tightly linked, or extremely tightly linked) an SCN resistance phenotype. In particular examples, the molecular markers may be SNP markers. Also described herein are methods of using nucleic acid molecular markers that are linked to an SCN resistance phenotype, for example and without limitation, to identify plants with an SCN resistance phenotype, to introduce an SCN resistance phenotype into new plant genotypes (e.g., through marker-assisted breeding or genetic transformation), and to cultivate plants that are likely to have an SCN resistance phenotype.

Further described are means for introducing an SCN phenotype to soybean and means for identifying plants having an SCN phenotype. In some examples, a means for introducing an SCN phenotype to soybean may be a marker that is linked (e.g., linked, tightly linked, or extremely tightly linked) to an SCN phenotype. In some examples, a means for identifying plants having an SCN phenotype may be a probe that specifically hybridizes to a marker that is linked (e.g., linked, tightly linked, or extremely tightly linked) to an SCN phenotype.

Also described herein are plants and plant materials that are derived from plants having an SCN phenotype as identified using molecular markers described herein. Thus, soybean plants that are produced by marker-assisted selection using one or more molecular marker(s) that are linked to an SCN resistance phenotype are described.

BRIEF DESCRIPTION OF THE FIGURES

FIGS. 1a and 1c include a list of QTLs associated with SCN resistance that have been reported in the SCN literature.

FIG. 8 includes clusters of 96 lines on three SNPs loci that showed co-segregation with the SCN resistance trait.

SEQUENCE LISTING

Figure 2A:
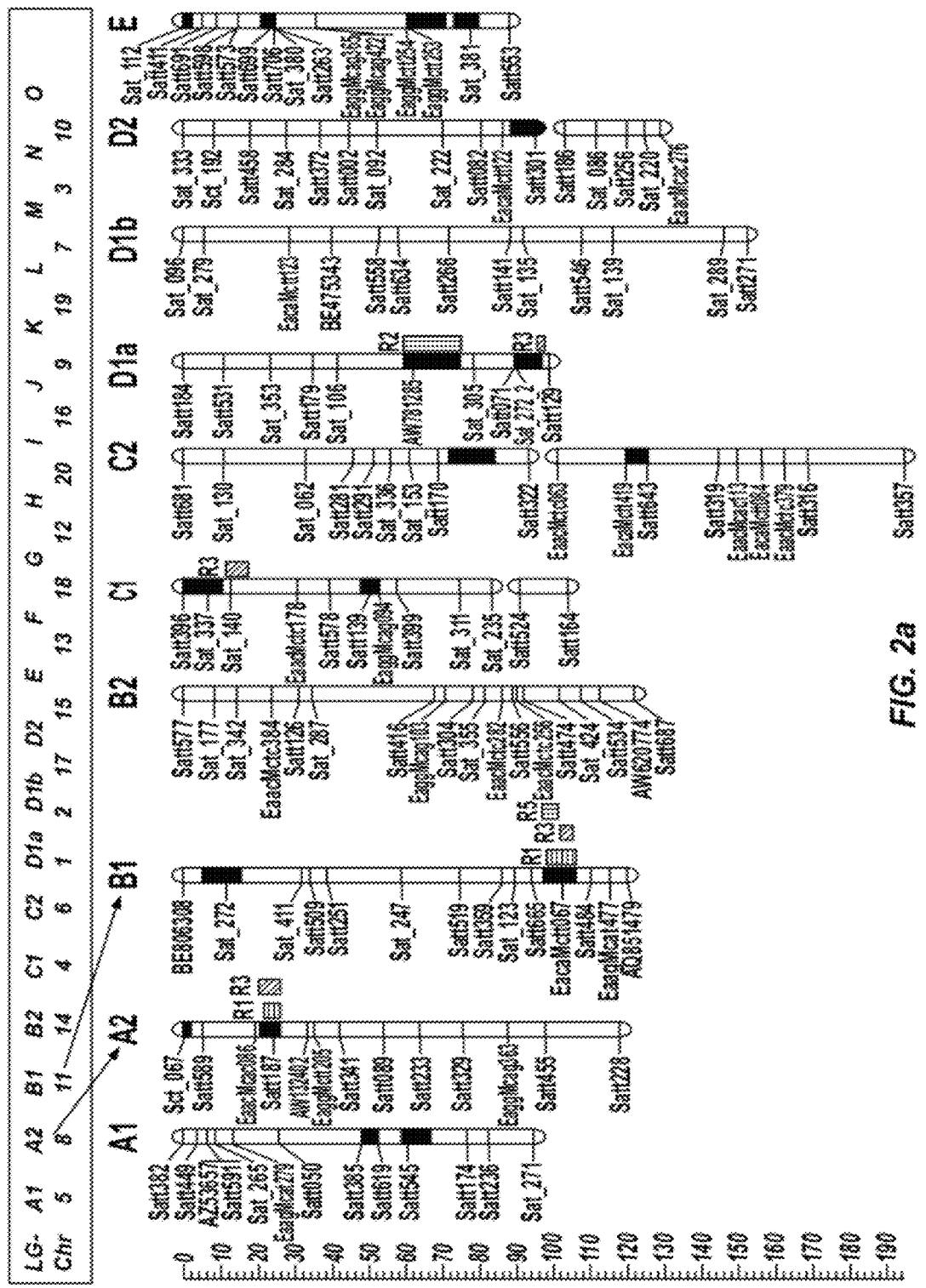
FIG. 2 includes a representation of the soybean genome, including chromosomes and linkage groups (LGs).

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand is understood to be included by any reference to the displayed strand. In the accompanying sequence listing:

SEQ ID NO:1 shows a primer sequence used in a KBiosciences Competitive Allele-Specific PCR (KASP™) SNP genotyping system assay that is specific for the rhg1-3995 allele: GAAGGTGACCAAGTTCATGCTGGAATTATGT-TGGGTTTTTTTTCTTTCTGT.

SEQ ID NO:2 shows a second primer sequence used in a KASP™ assay that is specific for the rhg1-3995 allele: GAAGGTCGGAGTCAACGGATTGAATTATGT-TGGGTTTT TTTTCTTTCTGG.

SEQ ID NO:3 shows a common reverse primer sequence used in a KASP™ assay for rhg1-3995: GCCCA-GAAAAAAGGGATAAATAACGGATA.

SEQ ID NO:4 shows a primer sequence used in a KASP™ assay that is specific for the NCSB_004074 allele: GAAGGTGACCAAGTTCATGCTATTATGTTGTAACA-CAA ATTTGCACCTCAT.

SEQ ID NO:5 shows a second primer sequence used in a KASP™ assay that is specific for the NCSB_004074 allele: GAAGGTCGGAGTCAACGGATTATGTTGTAACA CAAATTTGCACCTCAG.

SEQ ID NO:6 shows a common reverse primer sequence used in a KASP™ assay for NCSB_004074: CTATACAACTAAATCGTAATTCCATTGTAT.

SEQ ID NO:7 shows a primer sequence used in a KASP™ assay that is specific for the BARC_010889-01691 allele: GAAGGTGACCAAGTTCATGCTGAAAAAATAAAA TTGATCATCACATATGGTTAG.

SEQ ID NO:8 shows a second primer sequence used in a KASP™ assay that is specific for the BARC_010889-01691 allele: GAAGGTCGGAGTCAACGGATTGAAAAAAT AAAATTGATCATCACATATGGTTAA.

SEQ ID NO:9 shows a common reverse primer sequence used in a KASP™ assay for BARC_010889-01691: TAAGTGAGGGCAATGTATTAGTATYAAGTA.

SEQ ID NO:10 shows a marker NC SB 004074 sequence: CACGATTTTGTTGTGTTACATAAATTACTATACAACTAAATCGTAATTCCATTGTATTA C[A/C]TGAGGTGCAAATTTGTGTTACAACATAATTGTAATTTTATTGTACGATAAAAAC TATAAC.

SEQ ID NO:11 shows a marker BARC_010889-01691 sequence: CTCTTCACACCTTTAAGGAAGTTAGTACCATTCCACTATTCAAGTATTTTTTTTAATTC AAAATTATTAAGTGAGGGCAATGTATTAGTATNAAGTA [C/T] TAACCATATGTGATGA TCAATTTTATTTTTTCATGGCTTTGTCGAAAGTAACATTATATTGTGGTTTTAAATGAA AATCTGTGATTTGCAT.

SEQ ID NO:12 shows a marker rhg1-3995 sequence: TCTGATAACTATGACAGCATCTTCCAAGATAATGACTTCCAAGTTCCAACACTGGCTC TGTACATTTGAACTAATTTTATATCATTTATCTATTGTGATTGAAATATAAAATTGAAG TGATGTGAACAATACAAATCACATCTTGAATTAAAATATCTAACAACTGGAACAAATA AGAGGCCCAGAAAAAAGGGATAAATAACGGATAACAAG[A/C]CAGAAAGAAAAAAA ACCCAACATAATTCCAACTTCAAAATTCACTCAATAAAAAGTTTAACATGTAAATTTA CTTGGAAACAAAACTCATAAC-CAATAATAATAATAAAAAGAAATCAGTTTTATAG CATTAATTTGGGATGCTCTGCTTGTATGCAAATGGCACAACCTTACCCTCAAGATTGC AAAACACAGATGAGTAACAGATGCAATGTGAATCAATAAAAAGTATTGTTGCGTTGT TGATGACACAACCTTACTCATAAAAAATGCAT.

DETAILED DESCRIPTION

I. Overview of Several Embodiments

Particular embodiments include three exemplary SNP markers (rhg1-3995, BARC_010889_01691, and NCSB_004074) that show co-segregation with the soybean cyst nematode (SCN) resistance trait in 96 tested soybean lines. Markers that co-segregate with SCN resistance are linked to this trait and, therefore, may be useful in marker-assisted selection and breeding. Also disclosed herein is a strategy used to identify these three exemplary SNP markers linked to SCN resistance. The physical map positions of these three exemplary SNP markers in the *Glycine max* genome are provided. Using the three exemplary SNP markers described herein, a specific assay using KBiosciences Competitive Allele-Specific PCR (KASP™) SNP genotyping system was developed to rapidly and accurately identify plants carrying the SCN resistance trait. While embodiments of the invention are described with reference to three exemplary SNP markers linked to SCN resistance, those of skill in the art will appreciate that additional, equivalent markers may be identified using the techniques described herein. SNP markers linked to SCN resistance may be used, for example, in SCN genotyping to select SCN resistant individuals from soybean breeding populations.

Soybean cyst nematode (SCN) resistance is a very complex trait. SCN infestation may be caused by one or more different *Heterodera glycines* races, the resistance for each of which may require different resistant genes located on different linkage groups. See Table 1. The three markers disclosed in Table 1 are all located in linkage group G. The SCN resistance gene(s) in linkage group G is thought to be responsible for resistance to races 3 and 14.

The strategy described herein is used to identify markers in other linkage groups (for example, $A_2$, $B_1$, and I) that are linked to SCN resistance. Thus, methods for identifying such markers are also provided. The general strategy is also used to map other traits of interest. The strategy is more efficient than traditional mapping strategies and may be particularly useful in molecular breeding programs.

TABLE 1

| Sources of SCN resistance | | |
|---|---|---|
| Resistant Germplasm | *H. glycines* Races | Linkage groups (LG) |
| PI 88788 | 3, 14 | G |
| Peking | 1, 3, and 5 | G, A2, and B |
| PI 437654 | All | G (Rhg1), A2 (Rhg4), B, C1, L25, L26, M, and D1a |
| PI 90763 | 3 | |
| PI 438489B | 1, 2, 3, 5, and 14 | G, E, A1, B1, and C1 |
| PI 89772 | 1, 2, 3, and 5 | G, E, A1, C1, C2, and D1a |
| PI209332 | All | G (Rhg1), and A2 (Rhg4) |
| PUSCN14 | 3 | A, G, B, I, and F |
| Hartwig | 3 | |
| Forrest | 3 | G and A2 |
| Pyramid | 3, 14 (from PI 88788) | A2, D, and G |

II. Terms

Mapping population: As used herein, the term "mapping population" may refer to a plant population used for gene mapping. Mapping populations are typically obtained from controlled crosses of parent genotypes. Decisions on the selection of parents and mating design for the development of a mapping population, and the type of markers used, depend upon the gene to be mapped, the availability of markers, and the molecular map. The parents of plants within a mapping population must have sufficient variation for the trait(s) of interest at both the nucleic acid sequence and phenotype level. Variation of the parents' nucleic acid sequence is used to trace recombination events in the plants of the mapping population. The availability of informative polymorphic markers is dependent upon the amount of nucleic acid sequence variation.

Backcrossing: Backcrossing methods may be used to introduce a nucleic acid sequence into plants. The backcrossing technique has been widely used for decades to introduce new traits into plants. N. Jensen, Ed., *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

KBiosciences Competitive Allele-Specific PCR (KASP™) SNP genotyping system: KASP™ is a commercially available homogeneous fluorescent system for determining SNP genotypes (KBiosciences Ltd., Hoddesdon, UK). A KASP™ assay comprises an SNP-specific "assay mix," which contains three unlabelled primers, and a "reaction mix," which contains all the other required components, for example, a universal fluorescent reporting system. In addition to these mixes, the user provides, inter alia, a FRET-capable plate reader, microtiter plate(s), and DNA samples that contain about 5 ng/L DNA.

A typical KASP™ assay comprises the steps of: allele-specific primer design (e.g., using PRIMERPICKER™, which is a free service available through the internet at the KBiosciences website), preparation of reaction mix including the allele-specific primers, admixing the reaction mix to DNA samples in a microtiter plate, thermocycling, reading the plate in a fluorescent plate reader, and plotting and scoring the fluorescent data. Data from each sample are plotted together on a two-dimensional graph, where the x- and y-axes correspond to FAM and VIC fluorescence values. Samples having the same SNP genotype cluster together on the plot (i.e., A/A, A/a, and a/a). More technical information about the KASP™ system, including a guide of solutions to common problems, is obtainable from KBiosciences Ltd. (e.g., the *KASP™ SNP Genotyping System Reagent Manual*).

Linked, tightly linked, and extremely tightly linked: As used herein, linkage between genes or markers may refer to the phenomenon in which genes or markers on a chromosome show a measurable probability of being passed on together to individuals in the next generation. The closer two genes or markers are to each other, the closer to (1) this probability becomes. Thus, the term "linked" may refer to one or more genes or markers that are passed together with a gene with a probability greater than 0.5 (which is expected from independent assortment where markers/genes are located on different chromosomes). When the presence of a gene contributes to a phenotype in an individual, markers that are linked to the gene may be said to be linked to the phenotype. Thus, the term "linked" may refer to a relationship between a marker and a gene, or between a marker and a phenotype.

Because the proximity of two genes or markers on a chromosome is directly related to the probability that the genes or markers will be passed together to individuals in the next generation, the term "linked" may also refer herein to one or more genes or markers that are located within about 2.0 Mb of one another on the same chromosome. Thus, two "linked" genes or markers may be separated by about 2.1 Mb, 2.00 Mb, about 1.95 Mb, about 1.90 Mb, about 1.85 Mb, about 1.80 Mb, about 1.75 Mb, about 1.70 Mb, about 1.65 Mb, about 1.60 Mb, about 1.55 Mb, about 1.50 Mb, about 1.45 Mb, about 1.40 Mb, about 1.35 Mb, about 1.30 Mb, about 1.25 Mb, about 1.20 Mb, about 1.15 Mb, about 1.10 Mb, about 1.05 Mb, about 1.00 Mb, about 0.95 Mb, about 0.90 Mb, about 0.85 Mb, about 0.80 Mb, about 0.75 Mb, about 0.70 Mb, about 0.65 Mb, about 0.60 Mb, about 0.55 Mb, about 0.50 Mb, about 0.45 Mb, about 0.40 Mb, about 0.35 Mb, about 0.30 Mb, about 0.25 Mb, about 0.20 Mb, about 0.15 Mb, about 0.10 Mb, about 0.05 Mb, about 0.025 Mb, and about 0.01 Mb. Particular examples of markers that are "linked" to the SCN phenotype in soybean include nucleotide sequences on chromosome 18 of the soybean genome.

As used herein, the term "tightly linked" may refer to one or more genes or markers that are located within about 0.5 Mb of one another on the same chromosome. Thus, two "tightly linked" genes or markers may be separated by about 0.6 Mb, about 0.55 Mb, 0.5 Mb, about 0.45 Mb, about 0.4 Mb, about 0.35 Mb, about 0.3 Mb, about 0.25 Mb, about 0.2 Mb, about 0.15 Mb, about 0.1 Mb, and about 0.05 Mb.

As used herein, the term "extremely tightly linked" may refer to one or more genes or markers that are located within about 100 kb of one another on the same chromosome. Thus, two "extremely tightly linked" genes or markers may be separated by about 125 kb, about 120 kb, about 115 kb, about 110 kb, about 105 kb, 100 kb, about 95 kb, about 90 kb, about 85 kb, about 80 kb, about 75 kb, about 70 kb, about 65 kb, about 60 kb, about 55 kb, about 50 kb, about 45 kb, about 40 kb, about 35 kb, about 30 kb, about 25 kb, about 20 kb, about 15 kb, about 10 kb, about 5 kb, and about 1 kb. Particular examples of markers that are "extremely tightly linked" to the SCN phenotype in soybean include rhg1-3995, BARC_010889_01691, and NCSB_004074.

In view of the foregoing, it will be appreciated that markers linked to a particular gene or phenotype include those markers that are tightly linked, and those markers that are extremely tightly linked, to the gene or phenotype. Linked, tightly linked, and extremely tightly genetic markers of the SCN phenotype may be useful in marker-assisted breeding programs to identify SCN resistant soybean varieties, and to breed this trait into other soybean varieties to confer SCN resistance.

Locus: As used herein, the term "locus" refers to a position on the genome that corresponds to a measurable characteristic (e.g., a trait). An SNP locus is defined by a probe that hybridizes to DNA contained within the locus.

Marker: As used herein, a marker refers to a gene or nucleotide sequence that can be used to identify plants having a particular allele. A marker may be described as a variation at a given genomic locus. A genetic marker may be a short DNA sequence, such as a sequence surrounding a single base-pair change (single nucleotide polymorphism, or "SNP"), or a long one, for example, a microsatellite/simple sequence repeat ("SSR"). A "marker allele" refers to the version of the marker that is present in a particular individual.

The term marker as used herein may refer to a cloned segment of soybean chromosomal DNA (for example, a segment including rhg1-3995, BARC_010889_01691, or NCSB_004074), and may also or alternatively refer to a DNA molecule that is complementary to a cloned segment of soybean chromosomal DNA (for example, DNA complementary to a segment including rhg1-3995, BARC_010889_01691, or NCSB_004074).

In some embodiments, the presence of a marker in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the marker and additional, contiguous nucleotide sequence from the plant genome. This is referred to herein as a "contiguous probe." The additional, contiguous nucleotide sequence is referred to as "upstream" or "downstream" of the original marker, depending on whether the contiguous nucleotide sequence from the plant chromosome is on the 5' or the 3' side of the original marker, as conventionally understood. As is recognized by those of ordinary skill in the art, the process of obtaining additional, contiguous nucleotide sequence for inclusion in a marker may be repeated nearly indefinitely (limited only by the length of the chromosome), thereby identifying additional markers along the chromosome. All above-described markers may be used in some embodiments of the present invention.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: radiolabeling by nick translation, random priming, tailing with terminal deoxytransferase, or the like, where the nucleotides employed are labeled, for example, with radioactive $^{32}$P. Other labels which may be used include, for example and without limitation: Fluorophores (e.g., FAM and VIC), enzymes, enzyme substrates, enzyme cofactors, enzyme inhibitors, and the like. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) *Proc. Natl. Acad. Sci. USA* 80:4045-9.

A probe may contain a nucleotide sequence that is not contiguous to that of the original marker; this probe is referred to herein as a "noncontiguous probe." The sequence of the noncontiguous probe is located sufficiently close to the sequence of the original marker on the genome so that the noncontiguous probe is genetically linked to the same gene or trait (e.g., SCN resistance). For example, in some embodiments, a noncontiguous probe is located within 500 kb, 450 kb, 400 kb, 350 kb, 300 kb, 250 kb, 200 kb, 150 kb, 125 kb, 100 kb, 0.9 kb, 0.8 kb, 0.7 kb, 0.6 kb, 0.5 kb, 0.4 kb, 0.3 kb, 0.2 kb, or 0.1 kb of the original marker on the soybean genome.

A probe may be an exact copy of a marker to be detected. A probe may also be a nucleic acid molecule comprising, or consisting of, a nucleotide sequence which is substantially identical to a cloned segment of the subject organism's (for example, soybean) chromosomal DNA. As used herein, the term "substantially identical" may refer to nucleotide sequences that are more than 85% identical. For example, a substantially identical nucleotide sequence may be 85.5%, 86%, 87%, 88%, 89%, 90%, 91%, 92%, 93%, 94%, 95%, 96%, 97%, 98%, 99% or 99.5% identical to the reference sequence.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions. Thus, an oligonucleotide probe is "specifically hybridizable" to a maker allele if stable and specific binding occurs between the oligonucleotide probe and the marker allele (e.g., a SNP marker) under stringent hybridization conditions, but stable and specific binding does not occur between the oligonucleotide probe and the wild-type allele at the marker position.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Detailed instruction and guidance with regard to the hybridization of nucleic acids may be found, for example, in Sambrook et al. (ed.) *Molecular Cloning: A Laboratory Manual*, $2^{nd}$ ed., vol. 1-3, Cold Spring Harbor Laboratory Press, Cold Spring Harbor, N.Y., 1989, chapters 9 and 11; Hames and Higgins (eds.) *Nucleic Acid Hybridization*. IRL Press, Oxford, 1985; Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N Y, 1993; and Ausubel et al., Eds., Current Protocols in Molecular Biology, Chapter 2, Greene Publishing and Wiley-Interscience, N Y, 1995. Calculations regarding hybridization conditions required for attaining particular degrees of stringency are known to those of ordinary skill in the art from the foregoing references. Thus, the skilled person empirically knows which probes will bind specifically with a particular degree of stringency (a particular set of hybridization conditions) to a particular SNP marker within the context of its surrounding contiguous genomic nucleotide sequence.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

The following are representative, non-limiting hybridization conditions.

Very High Stringency (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Very High Stringency (detects sequence that share at least 90% sequence identity): Hybridization in 5×SSC buffer at 65° C. for 16 hours; wash twice in 2×SSC buffer at room temperature for 15 minutes each; and wash twice in 0.5 SSC buffer at 65° C. for 20 minutes each. According to the foregoing, the skilled person knows which probes will bind specifically with very high stringency (under the above-listed hybridization conditions) to a particular SNP marker within the context of its surrounding contiguous genomic nucleotide sequence.

Moderate Stringency (detects sequences that share at least 50% sequence identity): Hybridization in 6×SSC buffer at room temperature to 55° C. for 16-20 hours; wash at least twice in 2×-3×SSC buffer at room temperature to 55° C. for 20-30 minutes each.

With respect to all probes discussed, supra, the probe may comprise additional nucleic acid sequences, for example, promoters, transcription signals, and/or vector sequences. Any of the probes discussed, supra, may be used to define additional markers that are tightly linked to a gene involved in SCN resistance, and markers thus identified may be equivalent to exemplary markers named in the present disclosure, and thus are within the scope of the invention.

Marker-assisted breeding: As used herein, the term "marker-assisted breeding" may refer to an approach to breeding directly for one or more complex traits (e.g., SCN resistance). In current practice, plant breeders attempt to identify easily detectable traits, such as flower color, seed coat appearance, or isozyme variants that are linked to an agronomically desired trait. The plant breeders then follow the agronomic trait in the segregating, breeding populations by following the segregation of the easily detectable trait. However, there are very few of these linkage relationships available for use in plant breeding.

Marker-assisted breeding provides a time- and cost-efficient process for improvement of plant varieties. Several examples of the application of marker-assisted breeding involve the use of isozyme markers. See, e.g., Tanksley and Orton, eds. (1983) *Isozymes in Plant Breeding and Genetics*, Amsterdam: Elsevier. One example is an isozyme marker associated with a gene for resistance to a nematode pest in tomato. The resistance, controlled by a gene designated Mi, is located on chromosome 6 of tomato and is very tightly linked to Aps1, an acid phosphatase isozyme. Use of the Aps1 isozyme marker to indirectly select for the Mi gene provided the advantages that segregation in a population can be determined unequivocally with standard electrophoretic techniques; the isozyme marker can be scored in seedling tissue, obviating the need to maintain plants to maturity; and co-dominance of the isozyme marker alleles allows discrimination between homozygotes and heterozygotes. See Rick (1983) in Tanksley and Orton, supra.

Quantitative trait locus: As used herein, the term "Quantitative trait locus" (QTL) may refer to stretches of DNA that have been identified as likely DNA sequences (e.g., genes, non-coding sequences, and/or intergenic sequences) that underlie a quantitative trait, or phenotype, that varies in degree, and can be attributed to the interactions between two or more DNA sequences (e.g., genes, non-coding sequences, and/or intergenic sequences) or their expression products and their environment. Quantitative trait loci (QTLs) can be molecularly identified to help map regions of the genome that contain sequences involved in specifying a quantitative trait.

As used herein, the term "QTL interval" may refer to stretches of DNA that are linked to the genes that underlie the QTL trait. A QTL interval is typically, but not necessarily, larger than the QTL itself. A QTL interval may contain stretches of DNA that are 5' and/or 3' with respect to the QTL.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Single-nucleotide polymorphism: As used herein, the term "single-nucleotide polymorphism" (SNP) may refer to a DNA sequence variation occurring when a single nucleotide in the genome (or other shared sequence) differs between members of a species or paired chromosomes in an individual. Within a population, SNPs can be assigned a minor allele frequency that is the lowest allele frequency at a locus that is observed in a particular population. This is simply the lesser of the two allele frequencies for single-nucleotide polymorphisms. Different populations are expected to exhibit at least slightly different allele frequencies. Particular populations may exhibit significantly different allele frequencies. In some examples, markers linked to SCN resistance are SNP markers.

SNPs may fall within coding sequences of genes, non-coding regions of genes, or in the intergenic regions between genes. SNPs within a coding sequence will not necessarily change the amino acid sequence of the protein that is produced, due to degeneracy of the genetic code. An SNP in which both forms lead to the same polypeptide sequence is termed "synonymous" (sometimes called a silent mutation). If a different polypeptide sequence is produced, they are termed "non-synonymous." A non-synonymous change may either be missense or nonsense, where a missense change results in a different amino acid, and a nonsense change results in a premature stop codon. SNPs that are not in protein-coding regions may still have consequences for gene splicing, transcription factor binding, or the sequence of non-coding RNA. SNPs are usually biallelic and thus easily assayed in plants and animals. Sachidanandam (2001) Nature 409:928-33.

Trait or phenotype: The terms "trait" and "phenotype" are used interchangeably herein. For the purposes of the present disclosure, a trait of particular interest is SCN resistance.

III. QTL-Based Identification of Markers Linked to a Trait of Interest

A. Overview

In some embodiments, a trait (e.g., SCN resistance) is mapped using a strategy that is different from traditional mapping approaches. For example, a trait may be mapped according to a strategy that, for the sake of convenience, may be described as comprising four steps. In a first step, QTL interval target regions that correspond to a trait to be mapped may be determined. In a second step, markers (e.g., SNP markers) may be selected which are located within or near determined QTL intervals of the target genome (e.g., soybean genome). In a third step, specific primers may be designed that facilitate the genotyping of individual subjects with respect to selected markers. In particular examples, specific primers are designed for use in a KASP™ genotyping assay. In a fourth step, populations that show segregation for the trait may be screened using the specific primers to identify those markers that are linked to the trait.

B. Markers Linked to a Trait of Interest and the Identification Thereof

Determination of QTL Interval Target Regions and Identification of Markers.

QTLs may be determined by any technique available to those of skill in the art. For example, the physical positions of a QTL that corresponds to a particular trait of interest may be initially determined by reference to the location of genes that are known to contribute to the particular trait. In some embodiments, SCN resistance genes may be identified on at least four regions on chromosome 8, 11, 18, and 20, respectively. See, e.g., Concibido et al. (1996) Theor. Appl. Genet. 93:234-41, Concibido et al. (1997) Crop Sci. 37:258-64, Meksem et al. (1999) Theor. Appl. Genet. 99:1131-42, Qui et al. (1999) Theor. Appl. Genet. 98:356-64, Meksem et al. (2001) Mol. Breeding 7:63-71, Li et al. (2009) Mol. Breeding 24:63-76, Wu et al. (2009) Theor. Appl. Genet. 118: 1093-105; U.S. Pat. Nos. 5,491,081, 6,096,944, 6,162,967, 6,271,437, 6,284,948, 6,300,541, 6,538,175, 7,154,021, 7,485,770; U.S.S.N.s 20020129402, 20020144310, 20030005491, 20030135881, 20060225150, 20060253919, 20080072352, and 20090100537; and International PCT Publication Nos. WO1995020669A2, WO2001051627A2, and WO2008153804A2. In some embodiments, the initially identified QTLs are grouped or divided into a less complicated or extensive list of QTLs that may have boundaries in the genome that are the same or different than the boundaries of the initially identified QTLs.

In some embodiments, a region of DNA may be selected that is likely to contain markers that are linked to the QTL trait. This region may be referred to as a QTL interval. For example, a QTL interval may be a region of DNA that includes the QTL and additional genomic DNA that is near the QTL in either, or both, the 5' and 3' directions. In some embodiments, a QTL interval may be about 4 Mb, about 3.5 Mb, about 3 Mb, about 2.5 Mb, about 2 Mb, about 1.5 Mb, or about 1 Mb.

In particular embodiments, the target genome may be searched to identify markers that are physically located in, near, or between the QTLs and QTL intervals. If a reference map containing the location of known markers is available for the target genome, the reference map may be used to identify markers. Nucleic acid sequences of the target genome may also be searched, for example, by software such as BLAST™. In some embodiments, SNP markers may be identified. In some embodiments, markers may be identified that are physically located in, near, or between QTLs and QTL intervals of the soybean genome that correspond to the SCN resistance trait. In particular examples, identified SNP markers that are physically located in, near, or between QTLs and QTL intervals of the soybean genome that correspond to the SCN resistance trait may be selected from the group consisting of the markers listed in Table 2.

In other embodiments, particular markers may be selected from the identified markers that are physically located in, near, or between QTLs and QTL intervals that correspond to a trait of interest, which markers are polymorphic among the parental lines from which a mapping population will be generated. Polymorphism of a given marker among the parental lines is directly related to the ability to trace recombination events in a mapping population produced from the parental lines.

In particular examples, polymorphic markers among parental soybean lines are selected to screen SCN resistance mapping populations to determine which, if any, of the polymorphic markers are linked to the SCN resistance trait. Such markers may segregate so that one allele of the SNP marker appears exclusively in SCN resistant individuals, and the other allele of the SNP marker appears exclusively in SCN susceptible individuals. Mapping populations may be generated by crossing one variety that is SCN resistant with another variety that is SCN susceptible. In embodiments, a mapping population may comprise about 10, about 20, about 30, about 40, about 50, about 60, about 70, about 80, about 90, about 95, about 100, about 150, about 200, about 250, about 300, about 350, about 400, about 450, about 500, or more individuals. In some embodiments, SCN resistant soybean germplasm 98860-71 may be crossed with one or more SCN susceptible germplasm(s) (e.g., 75213 and 6CH026-035) to create mapping populations.

In some embodiments, the polymorphic markers may be single nucleotide polymorphisms (SNPs) linked to or within the gene or QTL corresponding to the SCN resistance trait of interest. These SNP markers may be detected by sequencing through the region containing the gene or QTL using any DNA sequencing methods known in the art, including but not limited to Sanger sequencing or high throughput sequencing ("Next Generation") methodologies that enable short or long sequence reads through the region of interest. In such embodiments, where genotyping by sequencing is used for the detection of SNP markers, primers corresponding to the flanking sequences of the region containing the SNPs in gene or QTL of interest may be used for the sequencing chemistries in order to sequence through the region of interest. In such embodiments, when different genotypes are used for sequencing through the region of interest for the detection of SNPs exemplified herein, other SNPs may be identified in addition to the SNPs exemplified herein. In such embodiments, the SNPs exemplified herein by themselves (individual SNPs) or in combination with other SNPs linked to exemplified sequences (haplotypes) may be utilized for differentiating genotypes towards marker assisted selection of plants for the SCN resistance trait of interest.

Primer Design and Linkage Screening.

Oligonucleotide probes (e.g., primers) may be designed to specifically detect markers that are physically located in, near, or between QTLs and QTL intervals that correspond to a trait of interest. In general, an oligonucleotide probe may be designed that specifically hybridizes to only one allele of a marker. In some embodiments, two oligonucleotide probes are designed to detect an SNP marker, such that each specifically hybridizes to the SNP allele to which the other probe does not specifically hybridize. As is understood by those of skill in the art, the length or composition of oligonucleotide probes for a particular marker may be varied according to established principles without rendering the probe non-specific for one allele of the marker.

In some embodiments, the oligonucleotide probes may be primers. In specific embodiments, primers may be designed to detect markers in a KASP™ genotyping assay. In particular embodiments, primers may be designed to detect markers linked to the SCN resistance phenotype in soybean using a KASP™ genotyping assay. In these and further embodiments, the detection system may provide a high-throughput and convenient format for genotyping individuals in a mapping population, which may greatly facilitate the identification of individuals carrying a particular gene or trait, and may also greatly facilitate the implementation or execution of a marker-assisted selection program.

In specific embodiments, the oligonucleotide probes may be primers designed to detect markers in a TAQMAN® genotyping assay. This method utilizes primers specific to the marker closely linked to the SCN resistance gene and fluorescent labeled probes containing a single nucleotide polymorphism (SNP). The SNP probe associated with resistance is labeled with a fluorescent dye such as FAM while the probe associated with susceptibility is labeled with a different fluorescent dye such as VIC. The data is analyzed as the presence or absence of a fluorescent dye signal. The detection system may provide a high-throughput and convenient format, such as multiplexing for genotyping individuals in a mapping population, which may greatly facilitate the identification of individuals carrying a particular gene or trait, and may also greatly facilitate the implementation or execution of a marker-assisted selection program.

Additional markers may be identified as equivalent to any of the exemplary markers named herein (e.g., markers listed in Table 3, such as, for example, rhg1-3995, BARC_010889_01691, and NCSB_004074), for example, by determining the frequency of recombination between the exemplary marker and an additional marker. Such determinations may utilize a method of orthogonal contrasts based on the method of Mather (1931), *The Measurement of Linkage in Heredity*, Methuen & Co., London, followed by a test of maximum likelihood to determine a recombination frequency. Allard (1956) *Hilgardia* 24:235-78. If the value of the recombination frequency is less than or equal to 0.10 (i.e., 10%), then the additional marker is considered equivalent to the particular exemplary marker for the purposes of use in the presently disclosed methods.

Markers that are linked to any and all SCN resistance genes may be identified in embodiments of the invention. Further, markers that control any and all of resistance contributing loci for all SCN HG races may be identified in embodiments of the invention.

A means for providing SCN resistance in soybean may be an SNP marker allele, the detection of which SNP marker allele in soybean plants belonging to, or derived from, germplasm 98860-71 provides at least a strong indication that the plant comprising the nucleic acid sequence has the SCN resistance phenotype. In some examples, a means for providing SCN resistance in soybean is a marker selected from the group consisting of the markers listed in Table 3. In particular examples, a means for providing SCN resistance in soybean is a marker selected from the group consisting of rhg1-3995, BARC_010889_01691, and NCSB_004074.

A means for identifying soybean plants having the SCN resistance phenotype may be a molecule that presents a detectable signal when added to a sample obtained from a soybean plant belonging to, or derived from, germplasm 98860-71 having the SCN resistance genotype, but which means does not present a detectable signal when added to a sample obtained from a soybean plant of belonging to, or derived from, germplasm 98860-71 that does not have the SCN resistance phenotype. Specific hybridization of nucleic acids is a detectable signal, and a nucleic acid probe that specifically hybridizes to an SNP marker allele that is linked to the SCN resistance phenotype may therefore be a means for identifying soybean plants having the SCN resistance phenotype. In some examples, a means for identifying soybean plants having the SCN resistance phenotype is a probe that specifically hybridizes to a marker that is linked to the SCN resistance phenotype.

C. Methods of Using Markers Linked to a Trait of Interest

Methods of using nucleic acid molecular markers that are linked to a trait of interest (e.g., SCN resistance in soybean) to identify plants having the trait of interest may result in a cost savings for plant developers, because such methods may eliminate the need to phenotype individual plants generated during development (for example, by crossing soybean plant varieties having SCN resistance with vulnerable plant varieties).

In particular embodiments, markers linked to SCN resistance in soybean may be used to transfer segment(s) of DNA that contain one or more determinants of SCN resistance. In particular embodiments, the markers may be selected from a group of markers comprising the markers listed in Table 3 and markers that are their equivalents. In some embodiments, a marker may be selected from the group consisting of rhg1-3995, BARC_010889_01691, and NCSB_004074. In some embodiments, a method for using markers linked to SCN resistance in soybean to transfer segment(s) of DNA that contain one or more determinants of SCN resistance may comprise analyzing the genomic DNA of two parent plants with probes that are specifically hybridizable to markers linked to the SCN resistance phenotype; sexually crossing the two parental plant genotypes to obtain a progeny population, and analyzing those progeny for the presence of the markers linked to the SCN resistance phenotype; backcrossing the progeny that contain the markers linked to the SCN resistance phenotype to the recipient genotype to produce a first backcross population, and then continuing with a backcrossing program until a final progeny is obtained that comprises any desired trait(s) exhibited by the parent genotype and the SCN resistance phenotype. In particular embodiments, individual progeny obtained in each crossing and backcrossing step are selected by SCN marker analysis at each generation. In some embodiments, analysis of the genomic DNA of the two parent plants with probes that are specifically hybridizable to markers linked to SCN resistance phenotype reveals that one of the parent plants comprises fewer of the linked markers to which the probes specifically hybridize, or none of the linked markers to which the probes specifically hybridize. In some embodiments, individual progeny obtained in each cross and/or backcross are selected by the sequence variation of individual plants.

In some embodiments, markers linked to the SCN resistance phenotype may be used to introduce one or more determinants of SCN resistance into a plant (e.g., soybean) by genetic transformation. In particular embodiments, the markers may be selected from a group of markers comprising the markers listed in Table 3 and markers that are their equivalents. In some embodiments, a method for introducing one or more determinants of SCN resistance into a plant by genetic recombination may comprise analyzing the genomic DNA of a plant (e.g., soybean) with probes that are specifically hybridizable to markers linked to the SCN resistance phenotype to identify one or more determinants of SCN resistance in the plant; isolating a segment of the genomic DNA of the plant comprising the markers linked to the SCN resistance phenotype, for example, by extracting the genomic DNA and digesting the genomic DNA with one or more restriction endonuclease enzymes; optionally amplifying the isolated segment of DNA; introducing the isolated segment of DNA into a cell or tissue of a host plant; and analyzing the DNA of the host plant with probes that are specifically hybridizable to markers linked to the SCN resistance phenotype to identify the one or more determinants of SCN resistance in the host plant. In particular embodiments, the isolated segment of DNA may be introduced into the host plant such that it is stably integrated into the genome of the host plant.

In some embodiments, markers that are linked to the SCN resistance phenotype may be used to introduce one or more determinants of SCN resistance into other organisms, for example, plants. In particular embodiments, the markers can be selected from a group of markers listed in Table 3 and markers that are their equivalents. In some embodiments, a method for introducing one or more determinants of SCN resistance into an organism other than soybean may comprise analyzing the genomic DNA of a plant (e.g., a soybean plant) with probes that are specifically hybridizable to markers linked to the SCN resistance phenotype to identify one or more determinants of SCN resistance in the plant; isolating a segment of the genomic DNA of the plant comprising the one or more determinants of SCN resistance, for example, by extracting the genomic DNA and digesting the genomic DNA with one or more restriction endonuclease enzymes; optionally amplifying the isolated segment of DNA; introducing the isolated segment of DNA into an organism other than soybean; and analyzing the DNA of the organism other than soybean with probes that are specifically hybridizable to markers linked to the SCN resistance phenotype to identify the one or more determinants of SCN resistance in the organism. In other embodiments, the isolated segment of DNA may be introduced into the organism such that it is stably integrated into the genome of the organism.

In some embodiments, markers that are linked to the SCN resistance phenotype may be used to identify a plant with one or more determinants of SCN resistance. In some embodiments, the plant may be a soybean plant. For example, the plant may be a soybean plant of germplasm 98860-71. In particular embodiments, nucleic acid molecules (e.g., genomic DNA or mRNA) may be extracted from a plant. The extracted nucleic acid molecules may then be contacted with one or more probes that are specifically hybridizable to markers linked to the SCN resistance phenotype. Specific hybridization of the one or more probes to the extracted nucleic acid molecules is indicative of the presence of one or more determinants of SCN resistance in the plant.

In some embodiments, markers that are linked to multiple determinants of SCN resistance may be used simultaneously. In other embodiments, markers that are linked to only one determinant of SCN resistance may be used. In specific examples, markers that are linked to SCN resistance with respect to one or more particular SCN HG races (e.g., race 1, race 2, race 3, race 5, and race 14) may be used simultaneously For example, a plurality of markers that are linked to SCN resistance with respect to different SCN HG races may be used simultaneously.

The following examples are provided to illustrate certain particular features and/or embodiments. These examples should not be construed to limit the disclosure to the particular features or embodiments described.

EXAMPLES

Example 1: Materials and Methods 24 soybean cultivars and SCN mapping parents were used to identify markers linked to the SCN resistance phenotype. 14 of the cultivars were SCN susceptible: 75110, 75155, 75163, 99630, 99726, 95895-755PRU, 99345-31, 75192, 75209, 75159, Essex, Williams 82, 75213, and 6CH026-035. 10 of the cultivars were SCN resistant: Maverick, Peking, PI209332, PI437654, 99811, 99294, Forrest, PI88788, PI437654, and 98860-71.

SCN bioassay: SCN bioassays were performed to generate phenotype information of mapping populations produced by crossing SCN resistant soybean variety 98860-71 with SCN susceptible soybean varieties 75213 and 6CH026-035. The phenotype information of the mapping population used is listed in Table 3. The industry does not have a uniform approach to categorizing resistance levels in soybean varieties. Therefore, resistance levels were categorized in terms of "SCN score:" SCN score 0-10=R (resistance); SCN score 10.1-29.9=MR (medium resistance); SCN score 30.0-59.9=MS (medium susceptible); and 60+=S (susceptible). SCN index values were determined by comparing testing lines to known susceptible and resistant lines. The index score was directly based on the percentage of SCN susceptibility observed for the sample. For example, if a testing line had 10 cysts on each of 9 plants, and Williams (susceptible) had 100 cysts on each of 9, then the testing line was categorized with an index of 10%. The final index was the average of the scores of the 9 plants.

KASP™ reactions: KASP™ primers were designed using PRIMERPICKER™ tool in KLIMS™ (KBioscience Laboratory Management System) by providing DNA sequences with SNPs. Three primers, A1 (Allele specific primer 1), A2 (Allele specific primer 2), and C (common reverse primer) were designed for each SNP sequence based on KASP™ chemistry. An assay mix of each KASP™ reaction was prepared as in the KASP™ SNP Genotyping System v2.0. The final reaction volume was 5 µL per reaction, including 1 µL DNA template (5 ng/µL), 2.5 µL 2× Reaction Mix, 0.06875 µL Assay mix, 0.04 µL 50 mM $MgCl_2$, and 1.39125 µL dd$H_2O$. The assay was carried out in 384-well format. The thermocycle conditions used during the assay were according to the manufacturer's instructions: 94° C. for 15 minutes; 20 cycles of 94° C. for 10 seconds, 57° C. for 5 seconds, and 72° C. for 10 seconds; and 22 cycles of 94° C. for 10 seconds, 57° C. for 20 seconds, and 72° C. for 40 seconds. PCR plates were centrifuged, and allele-specific FAM and VIC intensities were read on a spectrofluorometer (Tecan GENios™, Männedorf, Switzerland) at room temperature. Data were directly loaded and analyzed on KLIMS™ using Kluster Caller™.

Example 2: Identification of Physical Positions of QTLs and QTL Intervals that are Linked to SCN Resistance Genes QTLs that are involved in SCN resistance were initially identified by studying the SCN literature. The initially identified SCN-associated QTLs found in the SCN literature are listed in FIGS. 1a and 1b.

Figure 2B:
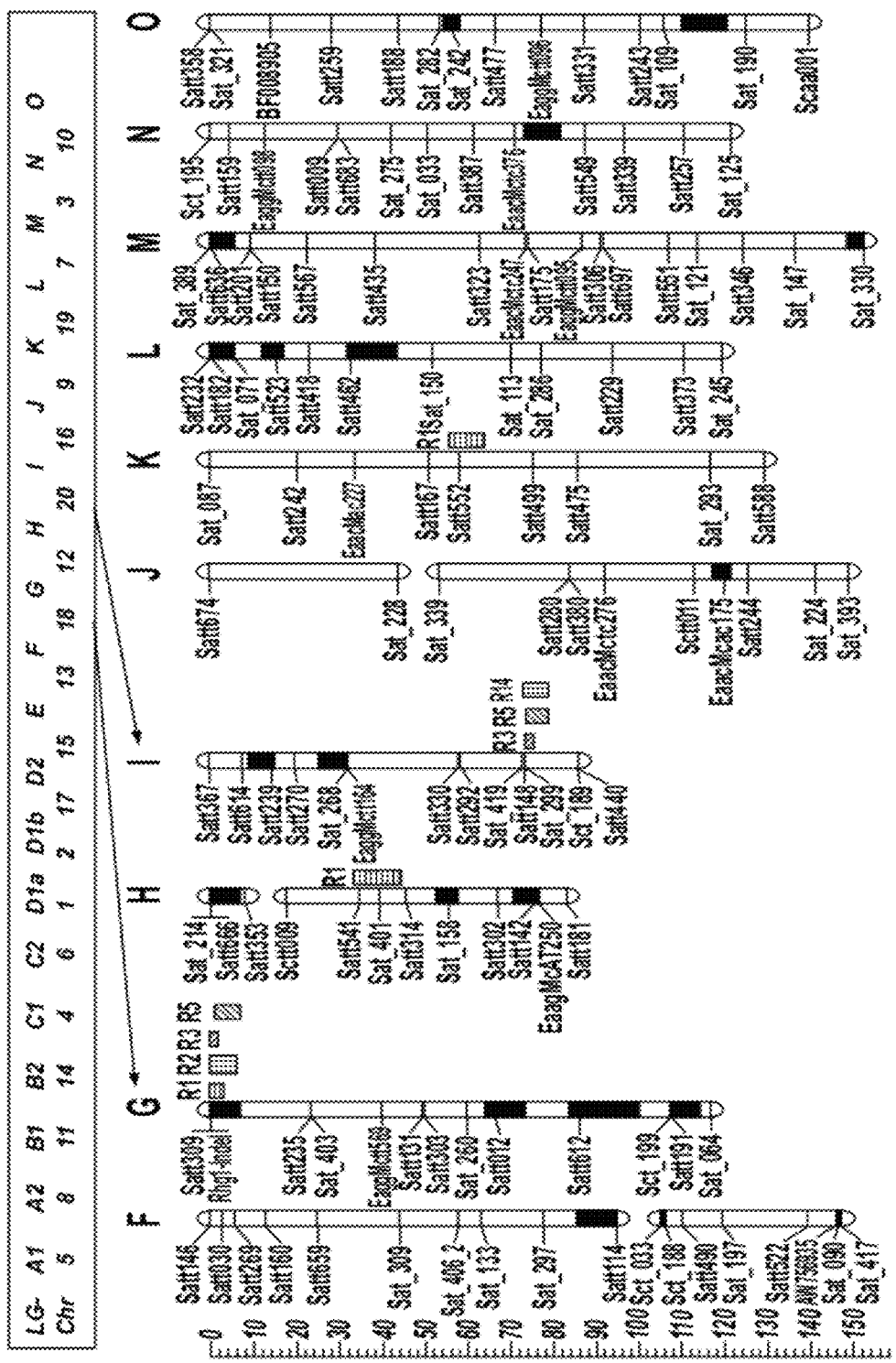
Figure 3:
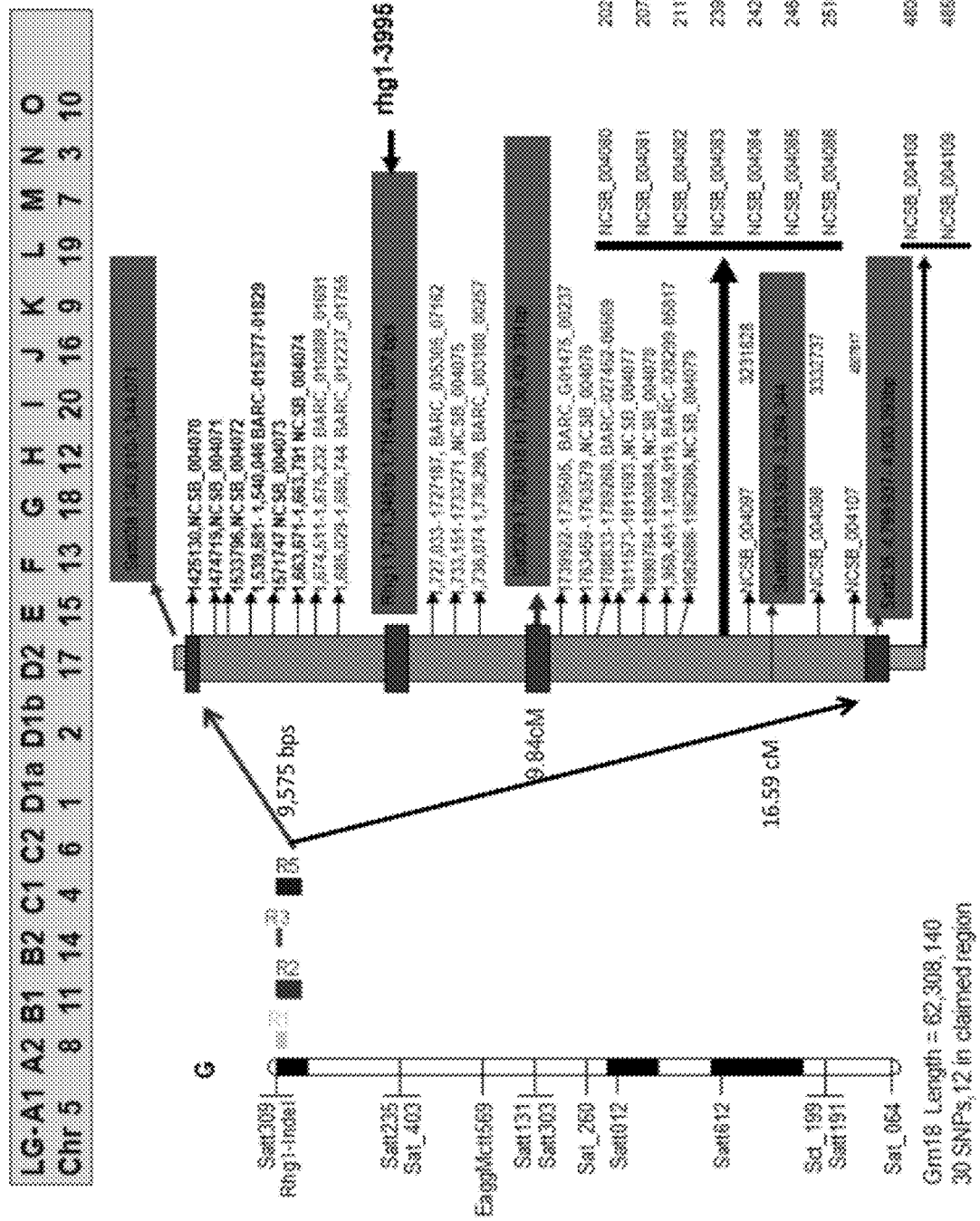
FIG. 3 includes a representation of soybean chromosome 18 (linkage group G), and QTLs and QTL intervals associated with SCN resistance and SNPs located therein.
Figure 4:
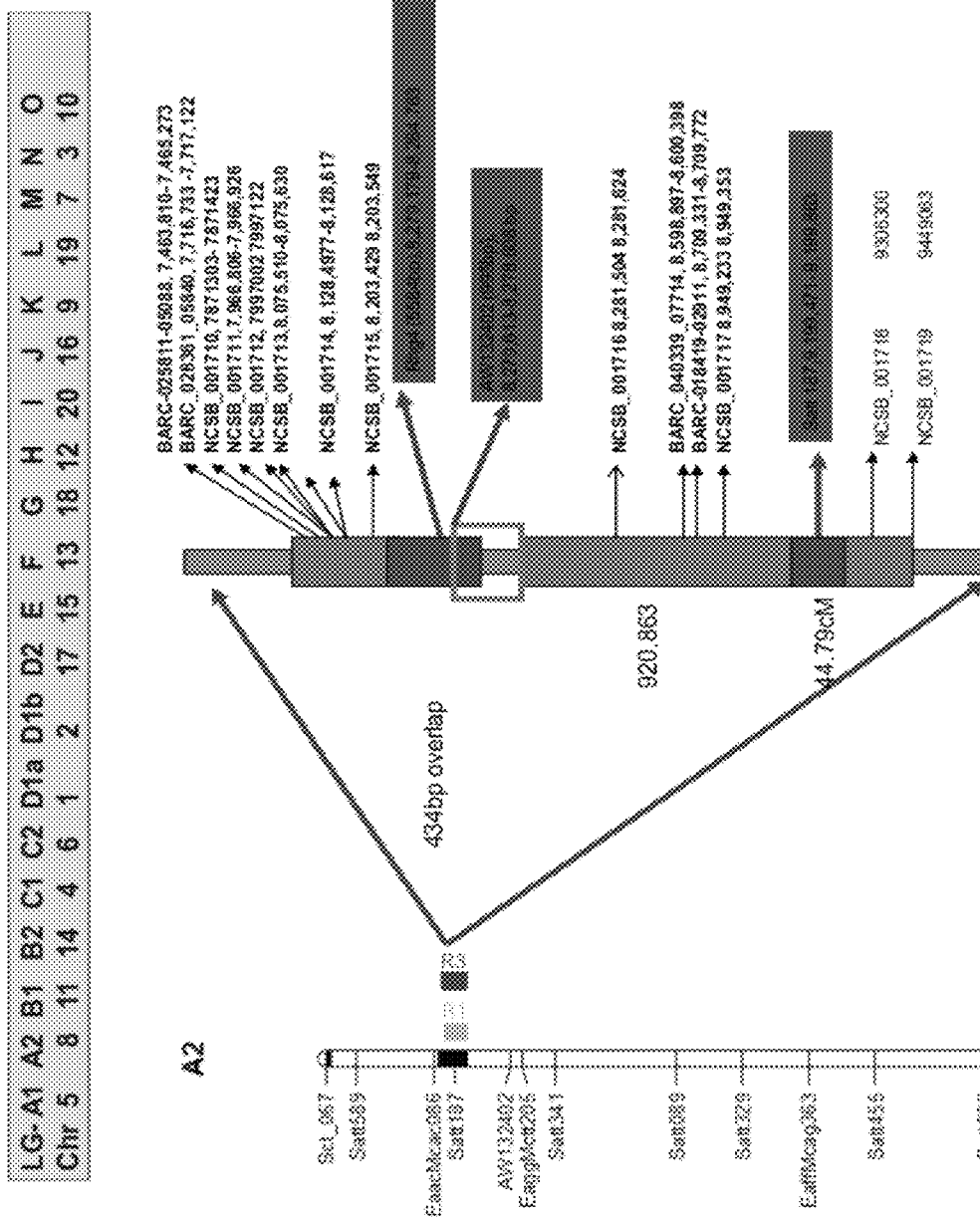
FIG. 4 includes a representation of soybean chromosome 8 (linkage group $A_2$), and QTLs and QTL intervals associated with SCN resistance and SNPs located therein.
Figure 5:
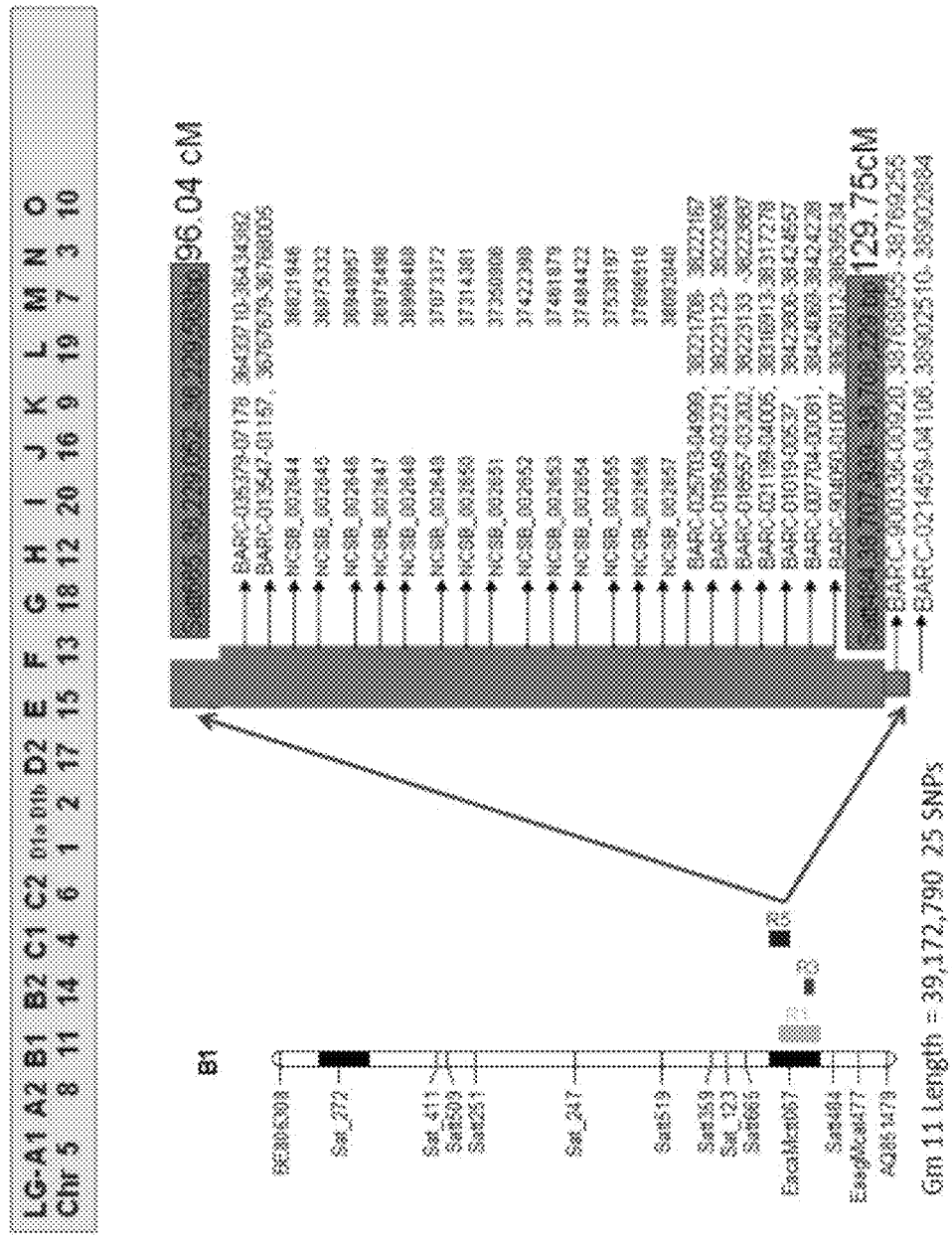
FIG. 5 includes a representation of soybean chromosome 11 (linkage group $B_1$), and QTLs and QTL intervals associated with SCN resistance and SNPs located therein.
Figure 6:
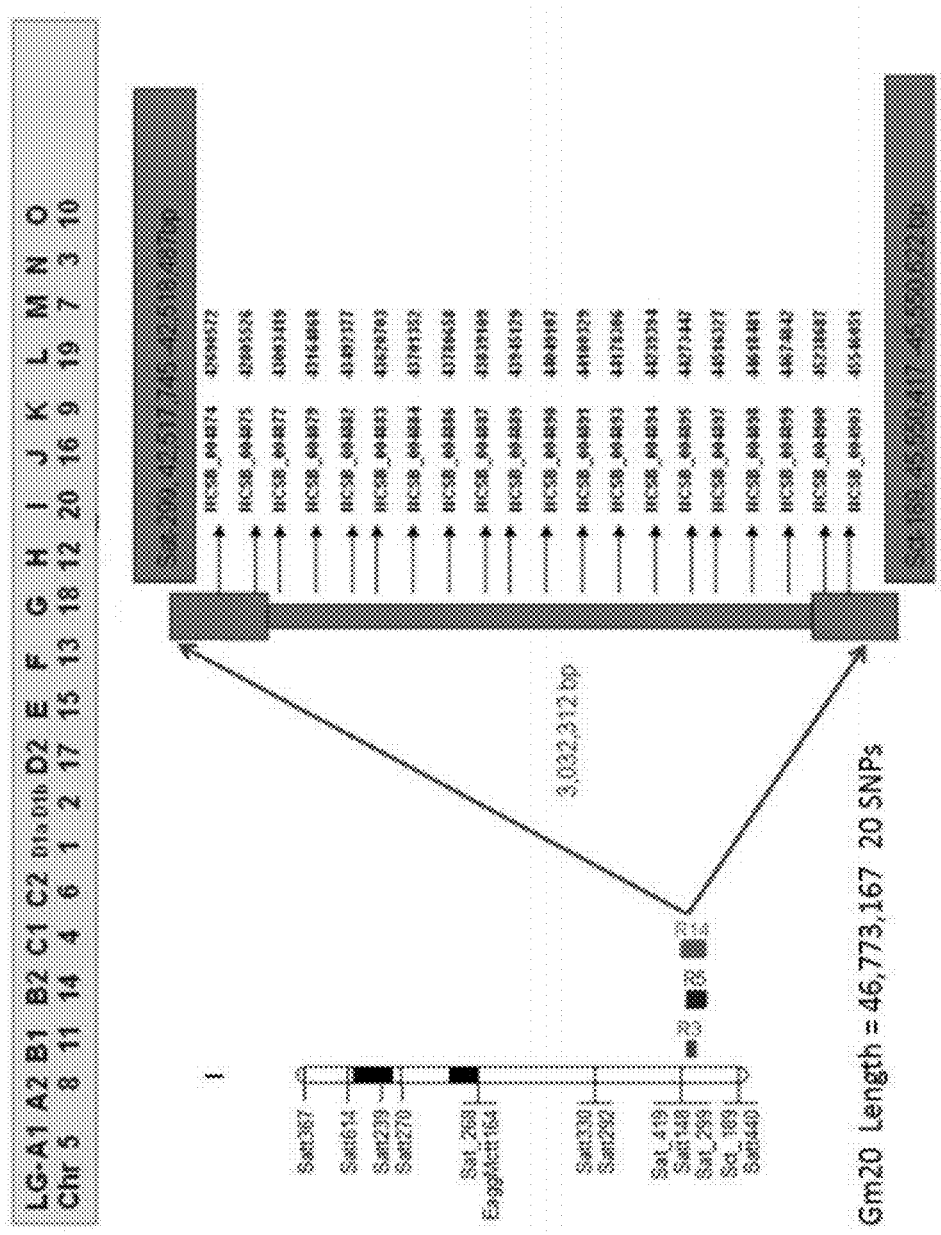
FIG. 6 includes a representation of soybean chromosome 20 (linkage group I), and QTLs and QTL intervals associated with SCN resistance and SNPs located therein.

From the list of QTLs that were initially identified in the SCN literature, several distinct QTL intervals that are involved in resistance to different SCN races were determined by reference to the soybean genome map. See, e.g., FIG. 2. For example, QTL intervals on linkage group (LG) G were determined as shown in FIG. 3; QTL intervals on LG A$_2$ were determined as shown in FIG. 4; QTL intervals on LG B$_1$ were determined as shown in FIG. 5; and QTL intervals on LG I were determined as shown in FIG. 6. Table 2 lists exemplary QTLs and their corresponding determined QTL intervals that are associated with resistance to different SCN races.

Example 3: Identification of SNP Markers that are Physically Located in/Near/Between the QTLs and QTL Intervals that are Linked to SCN Resistance Genes The soybean genome was searched using BLAST™ for SNP markers that are physically located in, near, or between the QTL intervals that were determined. It was hypothesized that some of these SNP markers may be linked to the SCN resistance phenotype. A total of 79 SNP markers were selected for an initial screen using 24 soybean lines (14 SCN susceptible and 10 SCN resistant) to determine which, if any, of these SNP markers are linked to the SCN resistance phenotype. 25 of the 79 markers were located on LG G, 12 of the markers were located on LG A2, 22 of the markers were located on LG B$_1$, and 20 of the markers were located on LG I. All of the 79 selected markers are listed in Table 2.

TABLE 2

List of the 79 SNPs for screening with 24 soybean lines

| Marker | SNP allele | Linkage group | Chromosome |
|---|---|---|---|
| BARC_018419_02911 | [C/T] | A2 | 8 |
| BARC_025811_05088 | [C/T] | A2 | 8 |
| BARC_040339_07714 | [A/G] | A2 | 8 |
| NCSB_001710 | [A/T] | A2 | 8 |
| NCSB_001716 | [T/C] | A2 | 8 |
| NCSB_001717 | [A/C] | A2 | 8 |
| NCSB_001718 | [A/G] | A2 | 8 |
| NCSB_001719 | [A/C] | A2 | 8 |
| BARC_007704_00081 | [T/A] | B1 | 11 |
| BARC_010169_00537 | [C/T] | B1 | 11 |
| BARC_013547_01157 | [A/T] | B1 | 11 |
| BARC_018557_03202 | [A/G] | B1 | 11 |
| BARC_018649_03221 | [C/T] | B1 | 11 |
| BARC_025703_04999 | [C/G] | B1 | 11 |
| BARC_035379_07178 | [G/T] | B1 | 11 |
| BARC_904050_01007 | [A/T] | B1 | 11 |
| NCSB_002644 | [A/G] | B1 | 11 |
| NCSB_002645 | [A/G] | B1 | 11 |
| NCSB_002646 | [A/G] | B1 | 11 |
| NCSB_002647 | [A/T] | B1 | 11 |
| NCSB_002648 | [T/G] | B1 | 11 |
| NCSB_002649 | [T/C] | B1 | 11 |
| NCSB_002650 | [C/G] | B1 | 11 |
| NCSB_002651 | [T/C] | B1 | 11 |
| NCSB_002652 | [T/C] | B1 | 11 |
| NCSB_002653 | [A/C] | B1 | 11 |
| NCSB_002654 | [A/C] | B1 | 11 |
| NCSB_002655 | [A/C] | B1 | 11 |
| NCSB_002656 | [A/G} | B1 | 11 |
| NCSB_002657 | [A/C] | B1 | 11 |
| BARC_003180_00257 | [C/T] | G | 18 |
| BARC_010889_01691 | [C/T] | G | 18 |
| BARC_012237_01755 | [A/C] | G | 18 |
| BARC_015377_01829 | [A/C] | G | 18 |
| BARC_027452_06569 | [A/T] | G | 18 |
| BARC_028299_05817 | [C/G] | G | 18 |
| BARC_035305_07162 | [A/T] | G | 18 |
| BARC_G01475_00237 | [A/C] | G | 18 |
| NCSB_004072 | [A/G] | G | 18 |
| NCSB_004073 | [A/G] | G | 18 |
| NCSB_004074 | [A/C] | G | 18 |
| NCSB_004078 | [A/G] | G | 18 |
| NCSB_004079 | [C/G] | G | 18 |
| NCSB_004080 | [C/G] | G | 18 |
| NCSB_004081 | [A/G] | G | 18 |
| NCSB_004082 | [T/C] | G | 18 |
| NCSB_004083 | [A/G] | G | 18 |
| NCSB_004084 | [A/T] | G | 18 |
| NCSB_004085 | [A/T] | G | 18 |
| NCSB_004086 | [A/T] | G | 18 |
| NCSB_004097 | [T/C] | G | 18 |
| NCSB_004098 | [T/C] | G | 18 |
| NCSB_004107 | [T/G] | G | 18 |
| NCSB_004108 | [A/C] | G | 18 |
| NCSB_004109 | [C/G] | G | 18 |
| rhg1_2564 | [G/—] | G | 18 |
| rhg1_3995 | [A/C] | G | 18 |
| rhg1_689 | [A/C] | G | 18 |
| rhg1_757 | [T/C] | G | 18 |
| NCSB_004874 | [A/G] | I | 20 |
| NCSB_004875 | [T/G] | I | 20 |
| NCSB_004877 | [A/T] | I | 20 |
| NCSB_004879 | [A/G] | I | 20 |
| NCSB_004882 | [A/T] | I | 20 |
| NCSB_004883 | [A/G] | I | 20 |
| NCSB_004884 | [T/G] | I | 20 |
| NCSB_004886 | [T/C] | I | 20 |
| NCSB_004887 | [T/G] | I | 20 |
| NCSB_004889 | [A/G] | I | 20 |
| NCSB_004890 | [T/C] | I | 20 |
| NCSB_004891 | [T/C] | I | 20 |
| NCSB_004893 | [T/C] | I | 20 |
| NCSB_004894 | [T/C] | I | 20 |
| NCSB_004895 | [A/G] | I | 20 |
| NCSB_004897 | [T/C] | I | 20 |
| NCSB_004898 | [A/T] | I | 20 |
| NCSB_004899 | [A/C] | I | 20 |
| NCSB_004900 | [A/T] | I | 20 |
| NCSB_004903 | [T/G] | I | 20 |

Example 4: KASP™ Assay Development

Initial screening of the 79 SNP markers in the parental 24 lines was performed using KASP™ genotyping assays. 75 of the SNP markers were validated.

21 SNP markers on LG G (Gm 18) were validated: NCSB_004072, BARC_015277_01929, NCSB_004073, NCSB_004074, NCSB_004075, NCSB_004076, NCSB_004077, NCSB_004078, NCSB_004079, NCSB_004080, NCSB_004081, NCSB_004082, NCSB_004083, NCSB_004084, NCSB_004085, NCSB_004086, NCSB_004097, NCSB_004098, NCSB_004107, NCSB_004108, and NCSB_004109.

12 SNP markers on LG A2 (Gm 08) were validated: BARC_025911_05089, BARC_019419_02921, NCSB_001710, NCSB_001711, NCSB_001712, NCSB_001713, NCSB_001714, NCSB_001715, NCSB_001716, NCSB_001717, NCSB_001718, and NCSB_001719.

22 SNP markers on LG B1 (Gm 11) were validated: NCSB_002644, NCSB_002645, NCSB_002646, NCSB_002647, NCSB_002648, NCSB_002649, NCSB_002650, NCSB_002651, NCSB_002652, NCSB_002653, NCSB_002654, NCSB_002655, NCSB_002656, NCSB_002657, BARC_007704_00091, BARC_010269_00537, BARC_904050_01007, BARC_019557_03202, BARC_018649_03221, BARC_025703_04999, BARC_013547_01157, and BARC_035379_07178.

20 SNP markers on LG I (Gm 20) were validated: NCSB_004974, NCSB_004975, NCSB_004977, NCSB_004979, NCSB_004882, NCSB_004883, NCSB_004884, NCSB_004886, NCSB_004887, NCSB_004889, NCSB_004880, NCSB_004882, NCSB_004883, NCSB_004884, NCSB_004885, NCSB_004887, NCSB_004888, NCSB_004899, NCSB_004900, and NCSB_004903.

Figure 7:
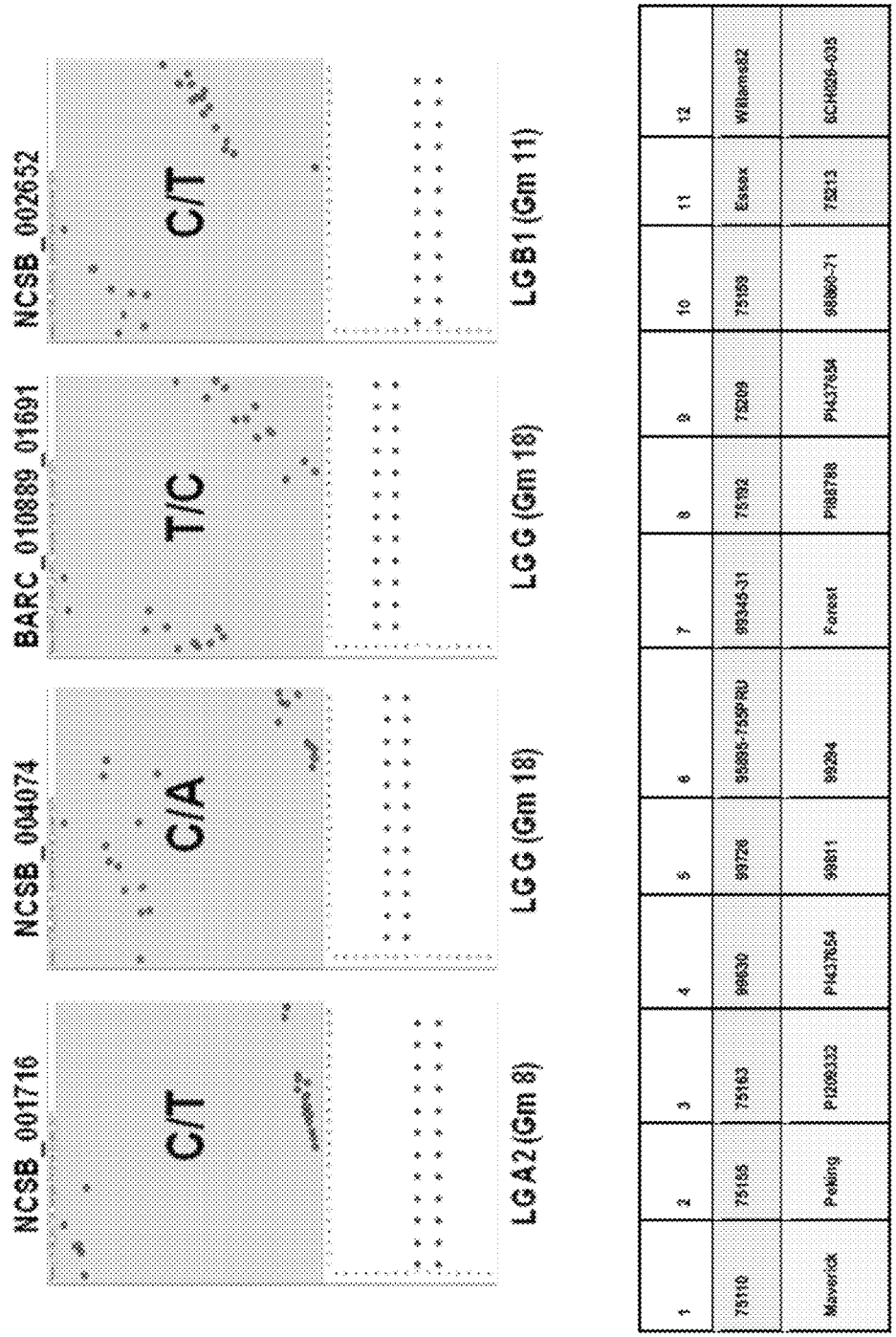
FIG. 7 includes clusters of 24 soybean SCN related cultivars or parental lines on four SNP loci. Also included is a table showing the 24 soybean cultivars and SCN mapping parents used. In the table, the first row of samples and the last two samples in the second row were SCN susceptible (green), and the first ten samples in the second row were SCN resistant (yellow). The last three samples in the second row were parental lines of two SCN mapping populations.
Figure 9:
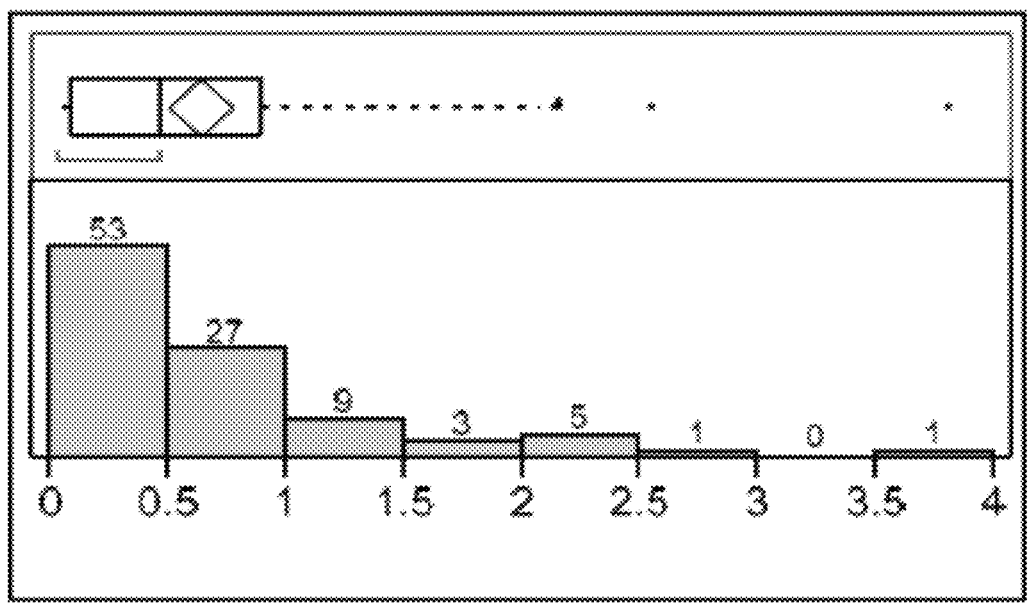
FIG. 9 includes the distribution of the SCN indexes assigned to mapping populations. The histogram shows a range from 0.01 to 3.8, with a mean of 0.63, and a median of 0.465.

The initial screening identified 44 of the SNP markers as polymorphic among the 24 parental lines. 24 polymorphic markers were selected (NCSB_001716 (LG A2), NCSB_002645 (B$_1$), NCSB_002646 (B$_1$), NCSB_002648 (B$_1$), NCSB_002651 (B$_1$), NCSB_002652 (B$_1$), NCSB_002654 (B$_1$), NCSB_002656 (B$_1$), BARC_013547_01157 (B$_1$), NCSB_004073 (G), NCSB_004074 (G), NCSB_004078 (G), NCSB_004080 (G), NCSB_004084 (G), NCSB_004085 (G), NCSB_004097 (G), NCSB_004109 (G), BARC_012237_01755 (G), rgh1-689 (G), rgh1-757 (G), rgh1-2564 (G), rgh1-3995 (G), and NCSB_004900 (I)) for further linkage testing with mapping populations produced by crossing SCN resistant soybean variety 98860-71 with SCN susceptible soybean varieties 75213 and 6CH026-035. FIG. 7 shows representative genotyping data from the KASP™ assay for four of the polymorphic markers.

15 of the SNP markers were polymorphic between SCN resistant and susceptible parents. These 15 polymorphic SNP markers were subsequently screened against 93 individuals in the mapping populations.

Of the fifteen SNP markers that were polymorphic among the parental lines that were tested against individuals of the mapping population, only three SNPs showed co-segregation with the SCN resistance trait: NCSB_004074, BARC_010889_01691, and rhg1-3995. FIG. 8. The KASP™ primer sequences that were used to genotype individuals for these three markers are listed in Table 3.

TABLE 3

The KASPar™ primer sequences of SNP markers

| | |
|---|---|
| rhg1-3995A1 | GAAGGTGACCAAGTTCATGCTGGAATTATGTTGGGTTTTTTTCTTTCTGT (SEQ ID NO: 1) |
| rhg1-3995A2 | GAAGGTCGGAGTCAACGGATTGAATTATGTTGGGTTTTTTTCTTTCTGG (SEQ ID NO: 2) |
| rhg1-3995C1 | GCCCAGAAAAAAGGGATAAATAACGGATA (SEQ ID NO: 3) |
| NCSB_004074A1 | GAAGGTGACCAAGTTCATGCTATTATGTTGTAACACAAATTTGCACCTCAT (SEQ ID NO: 4) |
| NCSB_004074A2 | GAAGGTCGGAGTCAACGGATTATGTTGTAACACAAATTTGCACCTCAG (SEQ ID NO: 5) |
| NCSB_004074C1 | CTATACAACTAAATCGTAATTCCATTGTAT (SEQ ID NO: 6) |
| BARC_010889-01691A1 | GAAGGTGACCAAGTTCATGCTGAAAAAATAAAATTGATCATCACATATGGTTAG (SEQ ID NO: 7) |
| BARC_010889-01691A2 | GAAGGTCGGAGTCAACGGATTGAAAAAATAAAATTGATCATCACATATGGTTAA (SEQ ID NO: 8) |
| BARC_010889-01691C1 | TAAGTGAGGGCAATGTATTAGTATYAAGTA (SEQ ID NO: 9) |

Using the genome nucleic acid sequence of soybean cultivar Williams 82 as a reference, BARC_010889_01691 is located on chromosome 18 at 1,674,511 bp; NCSB_004074 is located on chromosome 18 at 1,663,671 bp; and rgh1-3995 is located on chromosome 18 at 1,714,741 bp. All three linked markers (NSCB_004074, BARC_010889_01691, and rhg1-3995) are located either within the rhg1 locus (rgh1-3995), or close to it on linkage group G (BARC_010889_01691 and NCSB_004074).

For the resistant and medium resistant phenotypes, all three linked marker genotypes were congruent with the phenotype. With respect to the susceptible lines, BARC_010889_01691 had 5 mismatches with phenotypes, NSCB_004074 had 9 mismatches, and rhg1-3995 had 6 mismatches. See Table 4.

TABLE 4

Comparison of the phenotype score and genotype scores of 93 lines derived from two mapping populations plus 3 parents.

| Sample | SCN Resistance | SCN Score | rhg1_3995 | NCSB_004074 | BARC_010889_01691 |
|---|---|---|---|---|---|
| 40779 | R | 1.00 | C:C | A:A | T:T |
| 40785 | R | 1.60 | C:C | A:A | T:T |
| 29110 | R | 2.30 | C:C | A:A | T:T |
| 40780 | R | 2.30 | C:C | A:A | T:T |
| 29148 | R | 2.50 | C:C | A:A | T:T |
| 40781 | R | 2.50 | C:C | A:A | T:T |
| 40799 | R | 2.50 | C:C | A:A | T:T |
| 29226 | R | 3.10 | C:C | A:A | T:T |
| 40910 | R | 4.00 | C:C | A:A | T:T |
| 29040 | R | 4.10 | C:A | A:A | T:T |
| 40908 | R | 4.50 | C:C | A:A | T:T |
| 19152 | R | 4.70 | C:C | A:A | T:T |
| 29149 | R | 4.80 | C:C | A:A | T:T |
| 29023 | R | 5.60 | C:C | A:A | T:T |
| 40907 | R | 5.80 | C:C | A:A | T:T |
| 40959 | R | 6.10 | C:C | A:A | T:T |
| 29181 | R | 6.50 | C:C | A:A | T:T |
| 29151 | R | 6.60 | C:C | A:A | T:T |
| 19209 | R | 6.90 | C:C | A:A | T:T |
| 40989 | R | 7.10 | C:C | A:A | T:T |
| 29189 | R | 7.60 | C:C | A:A | T:T |
| 21692 | R | 8.30 | C:C | A:A | T:T |
| 29089 | R | 8.80 | C:C | A:A | T:T |
| 21553 | R | 9.00 | C:C | A:A | T:T |
| 40833 | R | 9.20 | C:C | A:A | T:T |
| 21642 | R | 9.60 | C:C | A:A | T:T |
| 29228 | R | 9.70 | C:C | A:A | T:T |
| 40957 | R | 9.80 | C:C | A:A | T:T |
| 29191 | MR | 10.2 | C:C | A:A | T:T |
| 40935 | MR | 10.7 | C:C | A:A | T:T |
| 98860-71(P1-R) | R/MR | 11.3 | C:C | A:A | T:T |
| 21648 | R/MR | 11.8 | C:C | A:A | T:T |
| 19155 | MR | 12.4 | C:C | A:A | T:T |
| 40808 | MR | 12.6 | C:C | A:A | T:T |
| 40940 | MR | 13.0 | C:C | A:A | T:T |
| 40831 | MR | 13.7 | C:C | A:A | T:T |
| 40932 | MR | 14.5 | C:C | A:A | T:T |
| 29180 | MR | 16.9 | C:C | A:A | T:T |
| 40937 | MR | 17.9 | C:C | A:A | T:T |
| 40958 | MR | 19.6 | C:C | A:A | T:T |
| 40936 | MR | 21.5 | C:C | A:A | T:T |
| 41022 | X | 22.7 | C:C | A:A | T:T |
| 19182 | MR | 23.3 | C:C | A:A | T:T |
| 40810 | X | 27.5 | C:C | A:A | T:T |
| 41015 | X | 27.6 | C:C | A:A | T:T |
| 29039 | MS | 31.70 | A:A | C:C | C:C |
| 29212 | MS | 37.50 | C:C | A:A | T:T |
| 40905 | X | 39.70 | A:A | A:A | C:C |
| 40834 | X | 46.50 | A:A | C:C | C:C |
| 40906 | MS | 46.60 | A:A | A:A | C:C |
| 41016 | MS | 46.80 | A:A | C:C | C:C |
| 29179 | MS | 48.10 | A:A | C:C | C:C |
| 29119 | MS | 59.50 | A:A | C:C | C:C |
| 29021 | MS | 59.80 | A:A | C:C | C:C |
| 29142 | S | 61.90 | A:A | C:C | C:C |
| 40939 | S | 66.40 | A:A | C:C | C:C |
| 41026 | S | 67.90 | C:C | C:C | C:C |
| 40909 | S | 68.90 | A:A | C:C | C:C |
| 29150 | S | 70.60 | A:A | C:C | C:C |
| 40942 | S | 71.20 | A:A | A:A | C:C |
| 40711 | S | 71.50 | C:C | A:A | T:T |
| 40931 | S | 73.80 | A:A | C:C | C:C |
| 21633 | S | 75.00 | C:C | A:A | T:T |
| 29190 | S | 79.70 | A:A | C:C | C:C |
| 29229 | S | 79.90 | A:A | C:C | C:C |
| 40938 | S | 80.10 | A:A | C:C | C:C |
| 40873 | X | 81.50 | C:C | A:A | T:T |
| 29222 | S | 81.90 | A:A | C:C | C:C |
| 40941 | S | 84.00 | A:A | C:C | C:C |
| 40934 | S | 85.70 | A:A | C:C | C:C |
| 29376 | S | 88.90 | A:A | C:C | C:C |
| 75213(P2-S) | S | 88.90 | A:A | C:C | C:C |
| 40990 | S | 90.10 | A:A | C:C | C:C |
| 29224 | S | 90.60 | A:A | C:C | C:C |

TABLE 4-continued

Comparison of the phenotype score and genotype scores of 93
lines derived from two mapping populations plus 3 parents.

| Sample | SCN Resistance | SCN Score | rhg1_3995 | NCSB_004074 | BARC_010889_01691 |
|---|---|---|---|---|---|
| 29399 | S | 93.50 | A:A | C:C | C:C |
| 40798 | X | 96.40 | A:A | A:A | C:C |
| 21693 | X | 98.00 | A:A | C:C | C:C |
| 21684 | X | 98.10 | A:A | C:C | C:C |
| 6CH026-035 (P3-S) | S | 101.20 | A:A | C:C | C:C |
| 41014 | S | 109.40 | A:A | C:C | C:C |
| 41027 | S | 125.60 | A:A | C:C | C:C |
| 29514 | S | 130.00 | A:A | C:C | C:C |
| 21688 | S | 133.90 | A:A | C:C | C:C |
| 40992 | S | 134.40 | A:A | C:C | C:C |
| 21700 | S | 134.60 | A:A | C:C | C:C |
| 40991 | S | 138.80 | A:A | C:C | C:C |
| 40782 | S | 147.00 | A:A | C:C | C:C |
| 29639 | S | 163.20 | A:A | C:C | C:C |
| 40783 | S | 178.20 | C:C | A:A | T:T |
| 40778 | S | 187.40 | A:A | C:C | C:C |
| 21683 | S | 204.40 | A:A | C:C | C:C |
| 40809 | S | 207.70 | A:A | C:C | C:C |
| 40835 | S | 212.90 | A:A | C:C | C:C |
| 40832 | S | 215.20 | A:A | C:C | C:C |
| 21694 | S | 254.90 | A:A | C:C | C:C |
| 21698 | S | 380.00 | A:A | C:C | C:C |

R = resistance; MR = medium resistance; S = susceptible; MS = medium susceptible; and X = inconsistency.

Once we have identified any susceptible genotypes with these 3 SNP markers, there is a 0% false negative rate. In other words, we can identify with perfect accuracy the SCN susceptible phenotype using the 3 markers. We also can predict the SCN resistant genotype with a "false positive" rate of about 10-18% (5 or 9 divided by 51, the total number of susceptible samples). Therefore, of the SCN resistant genotypes identified, only 5-9% of them would be expected to exhibit a SCN susceptible phenotype.

Example 5: SNP Markers in LG $A_2$, LG $B_1$, and LG I that are Linked to the SCN Resistance Phenotype The soybean genome is searched using BLAST™ for SNP markers that are physically located in, near, or between QTL intervals associated with SCN resistance on linkage groups $A_2$, $B_1$, and I. A list of SNP markers is produced by the BLAST™ search. A plurality of SNP markers are selected for an initial screen using SCN susceptible and SCN resistant soybean lines to determine which, if any, of these SNP markers in linkage groups $A_2$, $B_1$, and I are linked to the SCN resistance phenotype.

Initial screening of the selected SNP markers in the parental lines is performed using KASP™ genotyping assays. A set of the selected SNP markers are validated, a subset of which are identified as polymorphic among the parental lines. At least one of the polymorphic SNP markers is/are used for linkage testing with mapping populations produced by crossing an SCN resistant soybean variety with one or more SCN susceptible soybean varieties. One or more of these polymorphic SNP markers are screened against individuals in the mapping populations.

SNPs that co-segregate with the SCN resistance trait in individuals of the mapping populations are identified as markers on linkage groups $A_2$, $B_1$, and I that are linked to SCN resistance in the SCN resistant parent variety. The linked marker genotypes match the phenotypes observed in the individuals of the mapping population.

Example 6: SNP Markers Linked to the SCN Resistance Phenotype in Germplasm JTN-5109

A plurality of SNP markers that are physically located in, near, or between QTL intervals associated with SCN resistance (for example, SNP markers selected from the group of markers listed in Table 3) are selected for an initial screen using SCN resistant soybean variety JTN-5109 and SCN susceptible soybean lines to determine which, if any, of these SNP markers are linked to the SCN resistance phenotype in soybean variety JTN-5109.

Initial screening of the selected SNP markers in the parental lines is performed using KASP™ genotyping assays. A set of the selected SNP markers are validated, a subset of which are identified as polymorphic among soybean variety JTN-5109 and the SCN susceptible parental lines. At least one of the polymorphic SNP markers is/are used for linkage testing with mapping populations produced by crossing soybean variety JTN-5109 with one or more SCN susceptible soybean varieties. These one or more polymorphic SNP markers are screened against individuals in the mapping populations.

SNPs that co-segregate with the SCN resistance trait in individuals of the mapping populations are identified as markers that are linked to SCN resistance in soybean variety JTN-5109. The linked marker genotypes match the phenotypes observed in the individuals of the mapping population.

Example 7: SNP Markers that are Linked to the SCN Resistance Phenotype in HG Races Other than Race 3

Mapping populations are developed specifically for an HG race other than race 3 by crossing an SCN resistant soybean variety selected from the group consisting of PI 88788, Peking, PI 437654, PI 90763, PI 438489B, PI 89772, PI209332, PUSCN14, Hartwig, Forrest, and Pyramid with one or more SCN susceptible soybean varieties.

The soybean genome is searched using BLAST™ for SNP markers that are physically located in, near, or between QTL intervals associated with SCN resistance with respect to the specific HG race. A list of SNP markers is produced by the BLAST™ search. A plurality of SNP markers are selected for an initial screen using the selected SCN resistant soybean variety and SCN susceptible varieties to determine which, if any, of the SNP markers are linked to the SCN resistance phenotype with respect to the specific HG race.

Initial screening of the selected SNP markers in the parental lines is performed using KASP™ genotyping assays. A set of the selected SNP markers are validated, a subset of which are identified as polymorphic among the parental lines. At least one of the polymorphic SNP markers is/are used for linkage testing with mapping populations produced by crossing the selected SCN resistant soybean variety with one or more SCN susceptible soybean varieties. These one or more polymorphic SNP markers are screened against individuals in the mapping populations.

SNPs that co-segregate with the SCN resistance trait in individuals of the mapping populations are identified as markers that are linked to SCN resistance in the SCN resistant parent variety with respect to the specific HG race. The linked marker genotypes match the phenotypes observed in the individuals of the mapping population.

What may be claimed is:

1. An oligonucleotide probe selected from the group consisting of SEQ ID NO:1, SEQ ID NO:2, SEQ ID NO:3, SEQ ID NO:7, SEQ ID NO:8, and SEQ ID NO:9, wherein the probe comprises a label that is a fluorophore or $^{32}$P.

2. An oligonucleotide probe that is specifically hybridizable to a marker linked to the SCN resistance phenotype in soybean, wherein the probe is:
   an oligonucleotide that consists of SEQ ID NO:11, SEQ ID NO:12, or the complement or reverse complement of either of the foregoing,
   wherein the probe comprises a label that is a fluorophore or $^{32}$P.

3. A method for transferring a determinant of SCN resistance in a soybean variety, the method comprising:
   (a) sexually crossing a first parental plant having a donor genotype comprising the determinant of SCN resistance with a second parental plant having a recipient genotype to obtain a progeny plant population;
   (b) identifying from the progeny plant population a plant with genomic DNA that binds the oligonucleotide probe of claim 2 under very high stringency hybridization conditions, thereby determining the presence of the determinant of SCN resistance in the plant;
   (c) backcrossing the identified plant from the progeny population that comprises the determinant of SCN resistance to the recipient genotype to produce a next generation population;
   (d) determining if a member of the next generation population comprises genomic DNA that binds the oligonucleotide probe under very high stringency hybridization conditions and a desired trait from the recipient genotype; and
   (e) if no member of the next generation population comprises genomic DNA that binds the oligonucleotide probe under very high stringency hybridization conditions and the desired trait from the recipient genotype, repeating steps (c) and (d) until an individual is identified that comprises genomic DNA that binds the oligonucleotide probe under very high stringency hybridization conditions and the desired trait from the recipient genotype.

4. The oligonucleotide probe of claim 2, wherein the probe is an oligonucleotide that binds under very high stringency conditions to a reference polynucleotide or the perfect complement of the reference polynucleotide, wherein the reference polynucleotide consists of SEQ ID NO:11 comprising a thymine (T) at nucleotide position 98 of the reference polynucleotide, wherein the oligonucleotide probe does not bind under the very high stringency hybridization conditions to the reference polynucleotide comprising a cytosine (C) at nucleotide position 98 of the reference polynucleotide.

5. The oligonucleotide probe of claim 2, wherein the probe is an oligonucleotide that binds under very high stringency hybridization conditions to a second reference polynucleotide or the perfect complement of the second reference polynucleotide, wherein the second reference polynucleotide consists of SEQ ID NO:12 comprising a cytosine (C) at nucleotide position 214 of the second reference polynucleotide, wherein the oligonucleotide probe does not bind under the very high stringency hybridization conditions to the second reference polynucleotide comprising an adenine (A) at nucleotide position 214 of the second reference polynucleotide.

6. The method according to claim 3, wherein the probe is an oligonucleotide that binds under very high stringency conditions to a reference polynucleotide or the perfect complement of the reference polynucleotide, wherein the reference polynucleotide consists of SEQ ID NO:11 comprising a thymine (T) at nucleotide position 98 of the reference polynucleotide, wherein the oligonucleotide probe does not bind under the very high stringency hybridization conditions to the reference polynucleotide comprising a cytosine (C) at nucleotide position 98 of the reference polynucleotide.

7. The method according to claim 3, wherein the probe is an oligonucleotide that binds under very high stringency hybridization conditions to a second reference polynucleotide or the perfect complement of the second reference polynucleotide, wherein the second reference polynucleotide consists of SEQ ID NO:12 comprising a cytosine (C) at nucleotide position 214 of the second reference polynucleotide, wherein the oligonucleotide probe does not bind under the very high stringency hybridization conditions to the second reference polynucleotide comprising an adenine (A) at nucleotide position 214 of the second reference polynucleotide.

8. A method for introducing a determinant of SCN resistance in a soybean variety into a host soybean plant lacking the determinant of SCN resistance by genetic transformation, the method comprising:

analyzing the genomic DNA of a plant with the oligonucleotide probe of claim 2 to identify the determinant of SCN resistance in the plant, wherein binding of the probe to the genomic DNA of the plant confirms the presence of the determinant of SCN resistance in the plant;

isolating a segment of the genomic DNA of the plant that binds to the oligonucleotide probe under very stringent hybridization conditions; and introducing the isolated segment of genomic DNA into a host soybean plant lacking the determinant of SCN resistance.

9. The method according to claim 8, wherein the isolated segment of DNA is stably integrated into the genome of the host soybean plant.

10. The method according to claim 8, wherein the probe is an oligonucleotide that binds under very high stringency conditions to a reference polynucleotide or the perfect complement of the reference polynucleotide, wherein the reference polynucleotide consists of SEQ ID NO:11 comprising a thymine (T) at nucleotide position 98 of the reference polynucleotide, wherein the oligonucleotide probe does not bind under the very high stringency hybridization conditions to the reference polynucleotide comprising a cytosine (C) at nucleotide position 98 of the reference polynucleotide.

11. The method according to claim 8, wherein the probe is an oligonucleotide that binds under very high stringency hybridization conditions to a second reference polynucleotide or the perfect complement of the second reference polynucleotide, wherein the second reference polynucleotide consists of SEQ ID NO:12 comprising a cytosine (C) at nucleotide position 214 of the second reference polynucleotide, wherein the oligonucleotide probe does not bind under the very high stringency hybridization conditions to the second reference polynucleotide comprising an adenine (A) at nucleotide position 214 of the second reference polynucleotide.

* * * * *